US011827927B2

(12) United States Patent
Gormley et al.

(10) Patent No.: US 11,827,927 B2
(45) Date of Patent: *Nov. 28, 2023

(54) PREPARATION OF TEMPLATES FOR METHYLATION ANALYSIS

(71) Applicants: Illumina Cambridge Limited, Cambridge (GB); Massachusetts Institute of Technology, Cambridge, MA (US)

(72) Inventors: Niall Gormley, Essex (GB); Andreas Gnirke, Cambridge, MA (US); David Jaffe, Cambridge, MA (US); Harris Nusbaum, Cambridge, MA (US)

(73) Assignees: ILLUMINA CAMBRIDGE LIMITED, Cambridge (GB); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 135 days.

This patent is subject to a terminal disclaimer.

(21) Appl. No.: 17/178,125

(22) Filed: Feb. 17, 2021

(65) Prior Publication Data

US 2021/0277459 A1    Sep. 9, 2021

Related U.S. Application Data

(60) Continuation of application No. 15/867,283, filed on Jan. 10, 2018, now Pat. No. 10,954,554, which is a division of application No. 12/069,174, filed on Feb. 7, 2008, now Pat. No. 9,868,982.

(60) Provisional application No. 60/900,313, filed on Feb. 7, 2007.

(51) Int. Cl.
*C12Q 1/6855* (2018.01)
*C12Q 1/6809* (2018.01)
*C12Q 1/6827* (2018.01)

(52) U.S. Cl.
CPC ......... *C12Q 1/6855* (2013.01); *C12Q 1/6809* (2013.01); *C12Q 1/6827* (2013.01)

(58) Field of Classification Search
None
See application file for complete search history.

(56) References Cited

U.S. PATENT DOCUMENTS

| | | |
|---|---|---|
| 5,302,509 A | 4/1994 | Cheeseman |
| 5,652,126 A | 1/1997 | Lackey et al. |
| 5,674,743 A | 10/1997 | Ulmer |
| 5,786,146 A | 7/1998 | Herman et al. |
| 5,846,727 A | 12/1998 | Soper et al. |
| 5,871,917 A | 2/1999 | Duffy |
| 5,874,260 A | 2/1999 | Cleuziat et al. |
| 5,942,391 A | 8/1999 | Zhang et al. |
| 6,090,552 A | 7/2000 | Nazarenko et al. |
| 6,200,756 B1 | 3/2001 | Herman et al. |
| 6,214,556 B1 | 4/2001 | Olek et al. |
| 6,221,635 B1 | 4/2001 | Rovera et al. |
| 6,251,594 B1 | 6/2001 | Gonzalgo et al. |
| 6,265,171 B1 | 7/2001 | Herman et al. |
| 6,300,071 B1 | 10/2001 | Vuylsteke et al. |
| 6,331,393 B1 | 12/2001 | Laird et al. |
| 6,506,562 B1 | 1/2003 | Weissman et al. |
| 6,605,432 B1 | 8/2003 | Huang |
| 6,787,308 B2 | 9/2004 | Balasubramanian et al. |
| 7,037,650 B2 | 5/2006 | Gonzalgo et al. |
| 10,954,554 B2 * | 3/2021 | Gormley ............ C12Q 1/6809 |
| 2002/0110826 A1 | 8/2002 | Dattagupta |
| 2002/0137056 A1 | 9/2002 | Erikson et al. |
| 2002/0137086 A1 | 9/2002 | Olek et al. |
| 2002/0142309 A1 | 10/2002 | Dattagupta |
| 2003/0082600 A1 | 5/2003 | Olek et al. |
| 2003/0119025 A1 | 6/2003 | Olek et al. |
| 2003/0129620 A1 | 7/2003 | Olek et al. |
| 2003/0162194 A1 | 8/2003 | Olek et al. |
| 2003/0170684 A1 | 9/2003 | Fan |
| 2004/0023230 A1 | 2/2004 | Olek et al. |
| 2004/0038245 A1 | 2/2004 | Belinsky et al. |
| 2004/0072197 A1 | 4/2004 | Jones et al. |
| 2004/0086866 A1 | 5/2004 | Chernov et al. |
| 2004/0234960 A1 | 11/2004 | Olek et al. |
| 2004/0248090 A1 | 11/2004 | Olek et al. |
| 2004/0265814 A1 | 12/2004 | Distler et al. |
| 2005/0053937 A1 | 3/2005 | Berlin |
| 2005/0202490 A1 | 9/2005 | Makarov et al. |
| 2006/0094016 A1 | 5/2006 | Gormley |
| 2008/0207460 A1 | 8/2008 | Gormley |
| 2018/0237844 A1 | 8/2018 | Gormley et al. |

FOREIGN PATENT DOCUMENTS

| | | |
|---|---|---|
| EP | 1568786 | 8/2005 |
| EP | 1180548 | 11/2005 |

(Continued)

OTHER PUBLICATIONS

Ahern (The Scientist Jul. 24, 1995 vol. 9 Issue 15 p. 20) (Year: 1995).
U.S Advisory Action dated Jan. 9, 2020, in U.S. Appl. No. 15/867,283.
U.S. Restriction Requirement dated Feb. 7, 2019 in U.S. Appl. No. 15/867,283.
"Program Highlights", NIH, Epigenomics, 2015.
ENCODE Consortium, ENCODE Standards and Guidelines for Whole Genome Shotgun Bisulfite Sequencing (WGBS), httr2s://v,;ww.encodepro[ect.org/documer.ts/108d25•, 5-c053-4b 18-bc65-27e8f26d62c5/@@download/attachmer.t/!vletily:ICSeq_Standards Ef\C0DE3 EM.pdf (Jul. 2015).

(Continued)

*Primary Examiner* — Katherine D Salmon
(74) *Attorney, Agent, or Firm* — Fletcher Yoder P.C.

(57) ABSTRACT

The invention relates to a method of preparing and using a library of template polynucleotides suitable for use as templates in solid-phase nucleic acid amplification and sequencing reactions to determine the methylation status of the cytosine bases in the library. In particular, the invention relates to a method of preparing and analysing a library of template polynucleotides suitable for methylation analysis.

16 Claims, 16 Drawing Sheets
Specification includes a Sequence Listing.

(56) References Cited

FOREIGN PATENT DOCUMENTS

| EP | 0745690 | 10/2008 |
|---|---|---|
| GB | 2412170 | 9/2005 |
| WO | WO94/03624 | 2/1994 |
| WO | WO98/13523 | 4/1998 |
| WO | WO98/44151 | 10/1998 |
| WO | WO98/56952 | 12/1998 |
| WO | WO2000/18957 | 4/2000 |
| WO | WO2000/26401 | 5/2000 |
| WO | WO2000/47767 | 8/2000 |
| WO | WO2000/70090 | 11/2000 |
| WO | WO2001/57248 | 8/2001 |
| WO | WO2001/62961 | 8/2001 |
| WO | WO2001/77377 | 10/2001 |
| WO | WO2001/94544 | 12/2001 |
| WO | WO2002/00927 | 1/2002 |
| WO | WO2002/18649 | 3/2002 |
| WO | WO2002/50305 | 6/2002 |
| WO | WO2002/083705 | 10/2002 |
| WO | WO2004/051224 | 6/2004 |
| WO | WO2005/078121 | 8/2005 |
| WO | WO2005/090607 | 9/2005 |

OTHER PUBLICATIONS

Adessi, et al., "Solid Phase DNA amplification: characterisation of primer attachment and amplification mechanisms", Nucleic Acids Research 28, 2000, 1-8.
Beck, "Taking the measure of the methylome", Nature Biotechnology, vol. 28, No. 10, Oct. 2010, 1026-1028.
Bestor, "Gene silencing. Methylation meets acetylation.", Nature, 393 (6683), 1998,311-312.
Costello, et al., "Aberrant CpG-lsland methylation has non-random and tumour-type-specific patterns", Nat Genet 24(2):132-138 (2000), 2000, 032-138.
Costello, J F. "Methylation Matters", Journal of Medical Genetics, London, Great Britain, vol. 38., No. 5., May 2001 p. 285-303, XP008018005, 285-303.
Dahl, et al., "DNA methylation analysis techniques", Biogerontology, 4 (4):233-250 (2003).,2003, 233-250.
Dowen, et al., "Widespread dynamic DNA methylation in response to biotic stress", PNAS, Jun. 25, 2012, E2183-E2191.
Dubiley, et al., "Polymorphism analysis and gene detection by minisequencing on an array of gel-immobilized primers", Nucleic Acids Research 27, 1999, 1-6.
Eads, et al., "Methylight: a high-throughput assay to measure DNA methylation", Nucleic Acids Research, 28(8), e32, 2000, i-viii.
Feil, et al., "Methylation analysis on individual chromosomes: improved protocol for bisuphphite genomic sequencing", Nucleic Acids Res. 22 (4):695-696 (1994) 1994, 695-696.
Feinberg, et al., "Hypomethylation distinguishes genes of some human cancers from their normal counterparts", Nature. 301 (5895):89-92 (1983), 1983, 89-92.
Frommer, et al., "A genomic sequencing protocol that yields a positive display of 5-methylcytosine residues in individual DNA strands", Proc Natl Acad Sci USA, 89 (5):1827-1831 (1992), 1992, 1827-1831.
Gonzalgo, et al., "Identification and characterization of differentially methylated regions of genomic DNA by methylation-sensitive arbitrarily primed PCR", Cancer Res. 57 (4): 594-599 (1997),1997, 594-599.
Gonzalgo, et al., "Rapid quantitation of methylation differences at specific sites using methylation-sensitive single nucleotide primer extension (Ms-SNuPE)", Nucleic Acids Res. 25 (12):2529-2531 (1997), 1997, 2529-2531.
Gonzalgo, M. et al., "Quantitative methylation analysis using methylation sensitive single nucleotide primer extension (Ms-SNuPE)", Methods,27:128-133 (2002).
Goto, "Regulation of X-chromosome inactivation in development in mice and humans", Microbial. Mal. Biol. Rev. 62, 1998, 362-378.

Grunau, Christoph et al., "Meth Tools—a toolbox to visualize and analyze DNA methylation data", Nucleic Acids Research, 28 (5), 2000, 1053-1058.
Gu, et al., "Preparation of reduced representation bisulfate sequencing libraries for genome-scale DNA methylation profiling"; Nature Protocols, vol. 6, No. 4, 468-481, 2011.
Hammons, et al., "Specific site methylation in the 5'-flanking region of CYP1 A2 lnterindividual differences in human livers", Life Sci 69:839-845 (2001 ), 839-845.
Hanada, et al., "bcl-2-gene hypomethylation and high-level expression in B-cell chronic lymphocytic leukemia", Blood. 82 (6):1820-1828 (1993)., 1993, 1820-1828.
Herman, et al., "Inactivation of the CDKN2/p16/MTS1 gene is frequently associated with abberrant DNA methylation in all common human cancers", Cancer Res. 55 (20):4525-30 (1995), 1995, 4525-30.
Herman, et al., "Methylation-specific PCR: a novel PCR assay for methylation status of CpG islands", Proc Natl Acad Sci USA 93 (19):9821-9826 (1996), 1996, 9821-9826.
Hermanson, "Bioconjugate Techniques", San Diego Academic Press, 1996, 640-643.
Huang, et al., "Methylation profiling of CpG islands in human breast cancer cells.", Hum Mal Genet. 8 (3):459-470 (1990), 1999, 459-470.
Issa, et al., "Methylation of the oestrogen receptor CpG islands ageing and nepplasia in human colon", Nat Genet. 7 (4) 536-540 (1994)., 1994, 536-540.
Jones, et al., "Cancer epigenetics comes of age", Nature Genetics, 21 (2), 1999, 163-167.
Jones, DH., "A iterative and regenerative method for DNA sequencing", Biotechniques, vol. 22:939 (1997)., 1997, 939.
Kawai, et al., "Comparison DNA methylation patterns among cell lines by restriction landmark genomic scanning", Mal Cell Biol. 14 (11 ):7421-7427 (1994)., 1994, 7421-7427.
Kolata, "Project Sheds Light on What Drives Genes", the New York Times, Health, Feb. 18, 2015.
Kuleshov, et al., "Whole-genome haplotyping using long reads and statistical methods", Nature Biotechnology, vol. 32, No. 3, Mar. 2014, 261-270.
Kumar, "Rett and ICF syndromes: methylation moves into medicine", J. Biosci., 25(3),2000, 213-214.
Lander, et al., "Initial sequencing and analysis of the human genome", Nature, 409(6822), 2001, 860-921.
Lewin, et al., "The Mystique of Epigenetics", Cell 93:301-303 (1998), 1998, 301-303.
Lister, et al., "Highly Integrated Single-Base Resolution Maps of the Epigenome in *Arabidopsis*", Cell 133, May 2, 2008, 523-536.
Lister, "Hotspots of aberrant epigenomic reprogramming in human induced pluripotent stem cells", Nature, vol. 471, Mar. 3, 2011, 68.
Lister, R. et al., "Human DNA methylomes at base resolution show widespread epigenomic differences," Nature, Nov. 19, 2009; 462 (7271 ): 315-322.
Lizardi, "Mutation detection and single-molecule counting using isothermal rolling-circle amplification", Nature Genetics, vol. 19, 1998, 225-232.
Meaburn, et al., "Next generation sequencing in epigenetics: Insights and challenges", Seminars in Cell & Developmental Biology 23, 2012, 192-199.
Meissner, et al., Nucleic Acids Research, 33, 2005, 5868-5877.
Oakeley, "DNA methylation analysis: a review of current methodologies.", Pharm Thera 84: 389-400 (1999)., Sometimes mistaken for "Costello" with same citation, 1999, 389-400.
Otterson, et al., "CDKN2 gene silencing in lung cancer by DNA hypermethylation and kinetics of p161NK4 protein induction by 5-aza 2'deoxycytidine", Oncogene 11(6):1211-6 (1995), 1995, 1211-1216.
Paul, et al., "Cytosine methylation: quantitation by automated genomic sequencing and GENESCAN analysis", Biotechniques, US vol. 21 No. 1, 1996, 126-133.
Razin, et al., "CpG methylation, chromatin structure and gene silencing—A three-way connection", EMBO J., 17(17), 1998, 4905-4908.

(56) References Cited

OTHER PUBLICATIONS

Razin, et al., "DNA Methylation and embryogenesis", DnA Methylation: Molecular Biology and Biological Significance, 1993, 343-357.
Reik, et al., "Epigenetic reprogramming in mammalian development", Science, 293,2001, 1089-1093.
Rein, et al., "Identifying 5-methylcytosine and related modifications in DNA genomes", Nucleic Acids Res. 26 (10):2255-2264 (1998), 1998, 2255-2264.
Sasaki, et al., "DNA methylation and genomic imprinting in mammals", Exs. 64, 1993,469-486.
Schmitz, et al., "Patterns of population epigenomic diversity", Nature, vol. 495, 2013, 193-200.
Schulz, "DNA methylation in urological malignancies (review)", Int. J. Oneal. 13, 1998, 151-167.
Tanabe, et al., "Evaluation of a While-Genome Amplification Method Based on Adaptor-Ligation PCR of Randomly Sheared Genomic DNA", Genes, Chromosomes and Cancer, vol. 38, 2003, 168.
Taylor, et al., "The diagnostic significance of Myf-3 hypermethylation in malignant limphoproliferative disorders", Leukemia 15(4):583-589 (2001), 2001, 583-589.
Toyota, et al., "Identification of differentially methylated sequences in colorectal cancer by methylated CpG island amplification", Cancer Res. 59 (10):2307-2312 (1999), 1999, 2307-2312.
Trinh, et al., "DNA Methylation Analysis by Methylight Technology", Methods, 25, 2001, 456-462.
Urich, et al., "MethylC-seq library preparation for base-resolution wholegenome bisulfate sequencing", nature protocols, vol. .10, No. 3, 2015.
Walker, et al., "Multiplex strand displacement amplification (SDA) and detection of DNA sequences from *Mycobacterium tuberculosis* and other mycobacteria", Nucleic Acids Research 22, 1994, 2670-2677.
Walker, et al., "Strand displacement amplification—an isothermal, in vitro DNA amplification technique", NAR, 20, 1992, 1691-1696.
Walter, et al., "Strand displacement amplification as an in vitro model for rolling-circle replication: deletion formation and evolution during serial transfer", PNAS 91, 1994, 7937-7941.
Westin, et al., "Anchored multiplex amplification on a microelectric chip array", Nature Biotechnology 18, 2000, 199-204.
Yan, et al., "CpG island Arrays: an application toward deciphering epigenetic signatures of breast cancer", Clin. Cancer Res. 6:1432-1438 (2000),2000, 1432-1438.
Yan, et al., "Role of DNA methylation and histone acetylation in steroid receptor expression in breast cancer", J. Mammary Gland Biol. Neoplasia, 6(2), 2001, 183-192.
U.S. Notice of Allowance dated Nov. 18, 2020 issued in U.S. Appl. No. 15/867,283.
U.S. Final Office Action dated Oct. 22, 2019 issued in U.S. Appl. No. 15/867,283.
U.S. Office Action dated Jun. 29, 2020 issued in U.S. Appl. No. 15/867,283.
U.S. Office Action dated May 13, 2019 issued in U.S. Appl. No. 15/867,283.

* cited by examiner

FIG. 1A
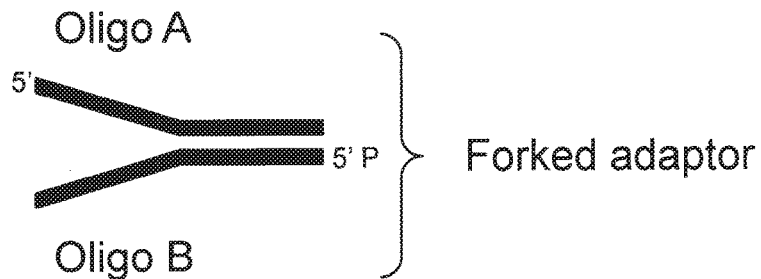
FIG. 1B
FIG. 1C
FIG. 1D
P = phosphate group
X, Y = surface capture functionality
All C bases in oligo A and B are methylated
FIG. 1E
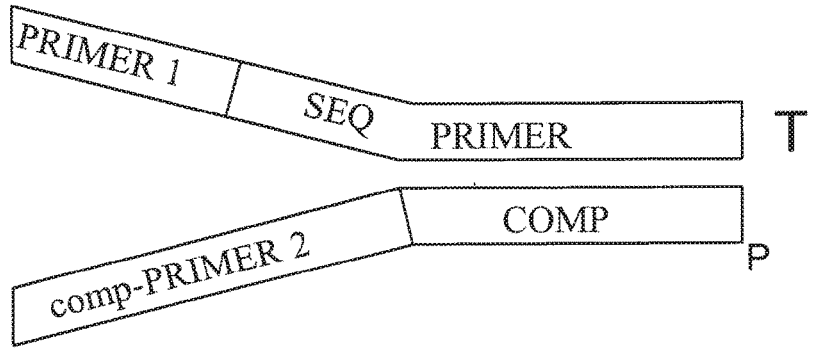

Forked adaptor

P = phosphate group

X, Y = surface capture functionality

All C bases in Oligo B and C are methylated

P = phosphate group

Z, W = modifications to prevent ligation

X, Y = surface capture functionality

All C bases on oligo D and E are methylated

SEQUENCE LISTING

<160> NUMBER OF SEQ ID NOS: 7

<210> SEQ ID NO 1
<211> LENGTH: 33
<212> TYPE: DNA
<213> ORGANISM: Artificial
<220> FEATURE:
<223> OTHER INFORMATION: Synthetic oligonucleotide
<220> FEATURE:
<221> NAME/KEY: misc_feature
<222> LOCATION: (4)..(4)
<223> OTHER INFORMATION: 5-methylcytosine
<220> FEATURE:
<221> NAME/KEY: misc_feature
<222> LOCATION: (12)..(12)
<223> OTHER INFORMATION: 5-methylcytosine
<220> FEATURE:
<221> NAME/KEY: misc_feature
<222> LOCATION: (14)..(14)
<223> OTHER INFORMATION: 5-methylcytosine
<220> FEATURE:
<221> NAME/KEY: misc_feature
<222> LOCATION: (20)..(20)
<223> OTHER INFORMATION: 5-methylcytosine
<220> FEATURE:
<221> NAME/KEY: misc_feature
<222> LOCATION: (21)..(21)
<223> OTHER INFORMATION: 5-methylcytosine
<220> FEATURE:
<221> NAME/KEY: misc_feature
<222> LOCATION: (24)..(24)
<223> OTHER INFORMATION: 5-methylcytosine
<220> FEATURE:
<221> NAME/KEY: misc_feature
<222> LOCATION: (27)..(27)
<223> OTHER INFORMATION: 5-methylcytosine
<220> FEATURE:
<221> NAME/KEY: misc_feature
<222> LOCATION: (30)..(30)
<223> OTHER INFORMATION: 5-methylcytosine

<400> SEQUENCE: 1
gatcggaaga gctcgtatgc cgtcttctgc ttg                            33

<210> SEQ ID NO 2
<211> LENGTH: 33
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (2)..(2)
<223> OTHER INFORMATION: 5-methylcytosine
<220> FEATURE:
<221> NAME/KEY: misc_feature
<222> LOCATION: (4)..(4)
<223> OTHER INFORMATION: 5-methylcytosine
<220> FEATURE:
<221> NAME/KEY: misc_feature
<222> LOCATION: (6)..(6)
<223> OTHER INFORMATION: 5-methylcytosine
<220> FEATURE:
<221> NAME/KEY: misc_feature
<222> LOCATION: (10)..(10)
<223> OTHER INFORMATION: 5-methylcytosine
<220> FEATURE:
<221> NAME/KEY: misc_feature
<222> LOCATION: (11)..(11)
<223> OTHER INFORMATION: 5-methylcytosine
<220> FEATURE:
<221> NAME/KEY: misc_feature
<222> LOCATION: (12)..(12)
<223> OTHER INFORMATION: 5-methylcytosine
<220> FEATURE:
<221> NAME/KEY: misc_feature

```
<222> LOCATION: (15)..(15)
<223> OTHER INFORMATION: 5-methylcytosine
<220> FEATURE:
<221> NAME/KEY: misc_feature
<222> LOCATION: (17)..(17)
<223> OTHER INFORMATION: 5-methylcytosine
<220> FEATURE:
<221> NAME/KEY: misc_feature
<222> LOCATION: (20)..(20)
<223> OTHER INFORMATION: 5-methylcytosine
<220> FEATURE:
<221> NAME/KEY: misc_feature
<222> LOCATION: (22)..(22)
<223> OTHER INFORMATION: 5-methylcytosine
<220> FEATURE:
<221> NAME/KEY: misc_feature
<222> LOCATION: (24)..(24)
<223> OTHER INFORMATION: 5-methylcytosine
<220> FEATURE:
<221> NAME/KEY: misc_feature
<222> LOCATION: (27)..(27)
<223> OTHER INFORMATION: 5-methylcytosine
<220> FEATURE:
<221> NAME/KEY: misc_feature
<222> LOCATION: (28)..(28)
<223> OTHER INFORMATION: 5-methylcytosine
<220> FEATURE:
<221> NAME/KEY: misc_feature
<222> LOCATION: (32)..(32)
<223> OTHER INFORMATION: 5-methylcytosine

<400> SEQUENCE: 2
acactctttc cctacacgac gctcttccga tct                            33

<210> SEQ ID NO 3
<211> LENGTH: 58
<212> TYPE: DNA
<213> ORGANISM: Artificial
<220> FEATURE:
<223> OTHER INFORMATION: Synthetic Oligonucleotide

<400> SEQUENCE: 3
aatgatacgg cgaccaccga gatctacact ctttccctac acgacgctct tccgatct  58

<210> SEQ ID NO 4
<211> LENGTH: 34
<212> TYPE: DNA
<213> ORGANISM: Artificial
<220> FEATURE:
<223> OTHER INFORMATION: Synthetic Oligonucleotide

<400> SEQUENCE: 4
caagcagaag acggcatacg agctcttccg atct                           34

<210> SEQ ID NO 5
<211> LENGTH: 30
<212> TYPE: DNA
<213> ORGANISM: Artificial
<220> FEATURE:
<223> OTHER INFORMATION: Synthetic Oligonucleotide
<220> FEATURE:
<221> NAME/KEY: misc_feature
<222> LOCATION: (10)..(11)
<223> OTHER INFORMATION: Nucleotides at positions 10 and 11 linked via
      diol

<400> SEQUENCE: 5
tttttttttt aatgatacgg cgaccaccga                                30

<210> SEQ ID NO 6
<211> LENGTH: 31
```

```
<212> TYPE: DNA
<213> ORGANISM: Artificial
<220> FEATURE:
<223> OTHER INFORMATION: Synthetic Oligonucleotide

<400> SEQUENCE: 6 ttttttttttt caagcagaag acggcatacg a                             31

<210> SEQ ID NO 7
<211> LENGTH: 33
<212> TYPE: DNA
<213> ORGANISM: Artificial
<220> FEATURE:
<223> OTHER INFORMATION: Synthetic Oligonucleotide

<400> SEQUENCE: 7
acactctttc cctacacgac gctcttccga tct                            33
```

PREPARATION OF TEMPLATES FOR METHYLATION ANALYSIS

STATEMENT REGARDING FEDERALLY SPONSORED RESEARCH OR DEVELOPMENT

This invention was made with government support under Grant No 3-U54-HG003067-03S2, awarded by the National Institute of Health. The United States government has certain rights in the invention.

CROSS REFERENCE TO RELATED APPLICATIONS

An Application Data Sheet is filed concurrently with this specification as part of the present application. Each application that the present application claims benefit of or priority to as identified in the concurrently filed Application Data Sheet is incorporated by reference herein in its entirety and for all purposes.

BACKGROUND

Several publications and patent documents are referenced in this application in order to more fully describe the state of the art to which this invention pertains. The disclosure of each of these publications and documents is incorporated by reference herein.

Molecular biology and pharmaceutical drug development now make intensive use of nucleic acid analysis. The most challenging areas are whole genome sequencing, single nucleotide polymorphism detection, screening and gene expression monitoring.

In many eukaryotes, between 10% and 30% of cytosine bases are modified by the enzymatic addition of a methyl group to the 5 position of the base. Although this modification does not interfere with the fidelity of DNA replication processes, it enables modulation of diverse cellular processes through protein interactions with hypo- or hypermethylated sequences. These methylated sequences are not randomly dispersed throughout a genome, but instead are almost exclusively found in repetitive CpG sequences in regulatory regions upstream of many genes. Methylation of these sequences is associated with repression of gene activity and can result in global changes to gene expression. For example, methylation plays a central role in the inactivation of one of the two X chromosomes in female cells, which is a prerequisite for ensuring that females do not produce twice the level of X linked gene products as males. Methylation also underlies the selective repression of either the maternally or paternally inherited copy of pairs of alleles in a process known as genetic imprinting. It also silences transposable elements whose expression would otherwise be deleterious to a genome.

Patterns of methylation in a genome are heritable because of the semi-conservative nature of DNA replication. During this process, the daughter strand, newly replicated on a methylated template strand is not initially methylated, but the template strand directs methyltransferase enzymes to fully methylate both strands. Thus methylation patterns carry an extra level of genetic information down through the generations in addition to that information inherited in the primary sequence of the four nucleotides.

Aberrant patterns of genomic methylation also correlate with disease states and are among the earliest and most common alteration found in human malignancies. Moreover, mistakes made during the establishment of methylation patterns during development underlie several specific inherited disorders. Consequently, there is a demand for high throughput approaches for profiling the methylation status of many genes in parallel both for research purposes and for clinical applications.

Many methods already exist for detecting the methylation of DNA and they can be broadly classified depending on the level of sequence-specific information they produce. On the simplest level, there are techniques that only yield information on overall levels of methylation within a genome. For example, methylated sequences can be separated from unmethylated sequences on reverse-phase HPLC due to the difference in hydrophobicity of DNase I treated DNA. Such methods are simple but do not provide any information regarding the sequence context of the methylation sites. Alternatively, pairs of restriction endonucleases that recognize the same sequence but have different sensitivities to cytosine methylation at that sequence can be used. Methylation at this sequence will render it refractory to cleavage by one enzyme, but sensitive to the other. If no cytosine bases are methylated in a sequence, both enzymes will produce identically sized restriction fragments. In contrast, if methylation is present, the enzymes will produce different sizes of fragments that can be distinguished by standard analytical techniques such as electrophoresis through agarose. If Southern blot analysis is subsequently performed and the bands probed with a labelled fragment from a gene of interest, then information on the sequence context of the methylation site can be investigated. These methods are limited because they are dependent on the availability of useful restriction enzymes and are confined to the study of methylation patterns among sequences that contain those restriction sites.

5-Methylcytosine (5mC) is a key epigenetic DNA modification in mammalian genomes. It occurs almost exclusively in the dinucleotide sequence mCpG and plays a central role in development and disease. Among the various methods for large-scale DNA-methylation analysis, only bisulfite sequencing affords single CpG resolution. Bisulfite deaminates unmethylated cytosine to uracil, while 5mC is not affected. Sequencing PCR-amplified bisulfite-converted DNA thus displays C and 5mC as T and C, respectively.

Methods that do not rely on sequence context but which can detect methylation at any chosen sequence are mainly based on the sodium bisulfite reaction. Under controlled conditions, this reagent converts cytosine to uracil while methyl-cytosine remains unmodified. If the treated DNA is then sequenced, the detection of a cytosine indicates that the cytosine is methylated because it would have been otherwise converted to a uracil.

Standard Sanger sequencing procedures have the disadvantage that only a limited number of sequencing reactions can be performed at the same time. Moreover, PCR amplification and sub-cloning may be necessary to produce sufficient quantities of DNA for sequencing, and both methods can introduce artifacts into the sequence, including changes in methylation.

Microarrays comprise molecular probes, such as nucleic acid molecules, arranged systematically onto a solid, generally flat surface or on a collection of beads or microspheres. Each probe site comprises a reagent such as a single stranded nucleic acid, whose molecular recognition of a complementary nucleic acid molecule leads to a detectable signal, often based on fluorescence. Microarrays comprising many thousands of probe sites can be used to monitor gene expression profiles for a large number of genes in a single experiment on a hybridisation based format.

Nucleic acid probes on microarrays are generally made in two ways. A combination of photochemistry and DNA synthesis allows base-by-base synthesis of the probes in situ. This is the approach pioneered by Affymetrix for growing short strands of around 25 bases. Their 'genechips' are commercially available and widely used (e.g., Wodlicka et al., 1997, *Nature Biotechnology* 15:1359-1367), despite the expense of making arrays designed for a particular experiment. Another method for preparing microarrays is to use a robot to spot small (nL) volumes of nucleic acid sequences onto discrete areas of the surface. Microarrays prepared in this manner have less dense features than Affymetrix arrays, but are more universal and cheaper to prepare (e.g., Schena et al., 1995, Science 270:467-470). The main drawback of all types of standard microarrays is the complex hardware required to achieve a spatial distribution of multiple copies of the same DNA sequence.

WO 98/44151 and WO 00/18957 both describe methods of forming polynucleotide arrays based on "solid-phase" nucleic acid amplification, which is analogous to a polymerase chain reaction wherein the amplification products are immobilised on a solid support in order to form arrays comprised of nucleic acid clusters or "colonies". Each cluster or colony on such an array is formed from a plurality of identical immobilised polynucleotide strands and a plurality of identical immobilised complementary polynucleotide strands. The arrays so-formed are generally referred to herein as "clustered arrays" and their general features will be further understood by reference to WO 98/44151 or WO 00/18957, the contents of both documents being incorporated herein in their entirety by reference.

As aforesaid, the solid-phase amplification methods of WO 98/44151 and WO 00/18957 are essentially a form of the polymerase chain (PCR) reaction carried out on a solid support. Like any PCR, these methods require the use of forward and reverse amplification primers capable of annealing to a template to be amplified. In the methods of WO 98/44151 and WO 00/18957, both primers are immobilised on the solid support at the 5' end. Other forms of solid-phase amplification are known in which only one primer is immobilised and the other is present in free solution (Mitra, R. D and Church, G. M., Nucleic Acids Research, 1999, Vol. 27, No. 24).

In common with all PCR techniques, solid-phase PCR amplification requires the use of forward and reverse amplification primers which include "template-specific" nucleotide sequences which are capable of annealing to sequences in the template to be amplified, or the complement thereof, under the conditions of the annealing steps of the PCR reaction. The sequences in the template to which the primers anneal under conditions of the PCR reaction may be referred to herein as "primer-binding" sequences.

PCR amplification cannot occur in the absence of annealing of the forward and reverse primers to primer binding sequences in the template to be amplified under the conditions of the annealing steps of the PCR reaction, i.e. if there is insufficient complementarity between primers and template. Some prior knowledge of the sequence of the template is, therefore, required before one can carry out a PCR reaction to amplify a specific template. The user generally must know the sequence of at least the primer-binding sites in the template in advance so that appropriate primers can be designed, although the remaining sequence of the template may be unknown. The need for prior knowledge of the sequence of the template increases the complexity and cost of solid phase PCR of complex mixtures of templates, such as genomic DNA fragments.

Certain embodiments of the methods described in WO 98/44151 and WO 00/18957 make use of "universal" primers to amplify templates comprising a variable template portion that it is desired to amplify, flanked 5' and 3' by common or "universal" primer binding sequences. The "universal" forward and reverse primers include sequences capable of annealing to the "universal" primer binding sequences in the template construct. The variable template portion may itself be of known, unknown or partially known sequence. This approach has the advantage that it is not necessary to design a specific pair of primers for each template to be amplified; the same primers can be used for amplification of different templates provided that each template is modified by addition of the same universal primer-binding sequences to its 5' and 3' ends. The variable template sequence can therefore be any DNA fragment of interest. An analogous approach can be used to amplify a mixture of templates, such as a plurality or library of template nucleic acid molecules (e.g. genomic DNA fragments), using a single pair of universal forward and reverse primers, provided that each template molecule in the mixture is modified by the addition of the same universal primer-binding sequences.

Such "universal primer" approaches to solid-phase amplification are advantageous since they enable multiple template molecules of the same or different, known or unknown sequence to be amplified in a single amplification reaction on a solid support bearing a single pair of "universal" primers. Simultaneous amplification of a mixture of templates of different sequences by PCR would otherwise require a plurality of primer pairs, each pair being complementary to each unique template in the mixture. The generation of a plurality of primer pairs for each individual template is not a viable option for complex mixtures of templates.

Adaptors that contain universal priming sequences can be ligated onto the ends of templates. The adaptors may be single-stranded or double-stranded. If double-stranded, they may have overhanging ends that are complementary to overhanging ends on the template molecules that have been generated with a restriction endonuclease. Alternatively, the double-stranded adaptors may be blunt ended, in which case the templates are also blunt ended. The blunt ends of the templates may have been formed during a process to shear the DNA into fragments, or they may have been formed by a "polishing" reaction, as would be well known to those skilled in the art, or may have been treated to give a single nucleotide overhang.

A single adaptor or two different adaptors may be used in a ligation reaction with templates. If a template has been manipulated such that its ends are the same, i.e. both are blunt ended or both have the same overhang, then ligation of a single compatible adaptor will generate a template with that adaptor on both ends. However, if two compatible adaptors, adaptor A and adaptor B, are used, then three permutations of ligated products are formed: template with adaptor A on both ends, template with adaptor B on both ends, and template with adaptor A on one end and adaptor B on the other end. This last product is, under some circumstances, the only desired product from the ligation reaction and consequently additional purification steps are necessary following the ligation reaction to purify it from the ligation products that have the same adaptor at both ends.

The above-mentioned prior art methods have inherent shortcomings that limit their utility with respect to a variety of genome wide analyses. Accordingly, the method of the present invention expands the spectrum of genome wide analyses that can be performed.

DETAILED DESCRIPTION

The present invention is directed to a method that uses a single methylated adaptor in a ligation reaction to generate a library of adaptor-target-adaptor polynucleotides for use in subsequent methylation analyses. The presence of methylated adaptors in these adaptor-target-adaptor polynucleotides facilitates treatment of such polynucleotides with bisulfite for the purposes of determining methylation status of cytosine bases in the target portion of the adaptor-target-adaptor polynucleotides. This directed investigation of methylation status of only the target portion of the adaptor-target-adaptor polynucleotides is made possible by the fact that the adaptors ligated onto the ends of the targets are fully methylated and are, therefore, resistant to bisulfite induced alterations. Thus, any unmethylated cytosine bases present in the adaptor-target-adaptor polynucleotides originate exclusively in the target nucleic acid portion of the polynucleotides and will be converted to uracils during bisulfite treatment. This feature of the present invention, therefore, facilitates directed analysis of target sequence methylation status and identification of the specific sequence context in which a methylated cytosine is found in the target sequence. The method can, moreover, be applied to preparing samples for amplification on a solid surface using surface-bound primer sequences, with no prior knowledge of the target sequences. The invention is, therefore, applicable to analysis of the methylation status of all cytosine bases across a whole genome sample (genome-wide analysis), as well as to more specific applications on smaller samples.

A first aspect of the invention relates to a method of analysing methylation status of cytosine bases in a nucleic acid, comprising:
  a. providing a sample of fragmented double stranded nucleic acid target fragments derived from said nucleic acid;
  b. ligating universal adaptors to the fragmented double stranded nucleic acid target fragments to produce adaptor-ligated double stranded nucleic acid target fragments comprising identical nucleic acid bases at each termini, wherein cytosine bases in said universal adaptors are methylated and said universal adaptors comprise a region of double stranded nucleic acids and at least one region of single stranded nucleic acids;
  c. treating the adaptor-ligated double stranded nucleic acid target fragments with a reagent that converts the non-methylated cytosine bases to uracil to produce a treated sample of adaptor-ligated double stranded nucleic acid target fragments;
  d. sequencing the treated adaptor-ligated double stranded nucleic acid target fragments;
  e. analysing the sequences of the treated sample to determine which cytosine bases were converted to uracil bases, thereby determining the methylation status of the nucleic acid.

A second aspect of the invention relates to methods of amplifying the treated samples. Thus, in a particular embodiment, the invention provides methods of amplifying the adaptor-ligated double stranded nucleic acid target fragments comprising identical nucleic acid bases at each termini.

A third aspect of the invention relates to methods for the solid-phase nucleic acid amplification of template polynucleotide molecules which comprises preparing a library of template polynucleotide molecules which have known sequences at their 5' and 3' ends using the method according to the first aspect of the invention and carrying out a solid-phase nucleic acid amplification reaction wherein said template polynucleotide molecules are amplified.

In a fourth aspect the invention provides a kit for use in preparing a 5' and 3' modified library of template polynucleotide molecules comprising known sequences at their 5' and 3' ends, the kit comprising methylated adaptor polynucleotides and oligonucleotide primers capable of annealing to the methylated adaptor polynucleotides.

SUMMARY

The invention relates to a method of preparing and using a library of template polynucleotides suitable for use as templates in solid-phase nucleic acid amplification and sequencing reactions to determine the methylation status of the cytosine bases in the library. In particular, the invention relates to a method of preparing and analysing a library of template polynucleotides suitable for methylation analysis.

DRAWINGS

FIGS. 1A-1D illustrate several examples of forked mismatch adaptors for use in the method of the invention, specifically depicting different overhanging or blunt end structures permissible at the "ligatable" end of the adaptor. FIG. 1E schematically illustrates the sequence components of the two partially complementary strands (denoted oligo A and oligo B) which form the universal forked adaptor when annealed. Oligo A and Oligo B are prepared with all the cytosine bases in the methylated form. The 5' end of oligo B is complementary (COMP) to a part of the SEQ PRIMER sequence in oligo A. Oligo A includes a single "T" nucleotide overhang at the 3' end. The 5' end of oligo A is phosphorylated. P represents a phosphate group; X and Y represent surface capture functionalities.

FIG. 2A illustrates one embodiment of the method of the invention based on use of the universal forked adaptors illustrated in FIGS. 1A-1E. The fragmented double stranded nucleic acid target fragments are ligated to the forked adaptors and then split into two portions, one of which is treated with sodium bisulfite. Both portions are then amplified and sequenced to determine the differences between the treated and untreated portions. FIG. 2B depicts the steps of fragmenting a complex sample such as genomic DNA to generate a plurality of target duplex fragments, ligation of the target duplex fragments to mismatch (forked) adaptors to generate adaptor-template constructs and removal of unbound adaptors. The forked adaptor may include a biotin group at the 5' end, which is not ligated to the target fragment, to facilitate solid-phase capture of the adaptor-target constructs, e.g. onto streptavidin magnetic beads. FIG. 2C depicts an initial primer extension reaction in which primers are annealed to mismatch adaptor regions on each strand of an adaptor-target construct and extended to generate extension products complementary to each strand of the adaptor-target construct. For simplicity, the ligation and primer extension steps are illustrated for a single adaptor-target construct.

Figure 5:
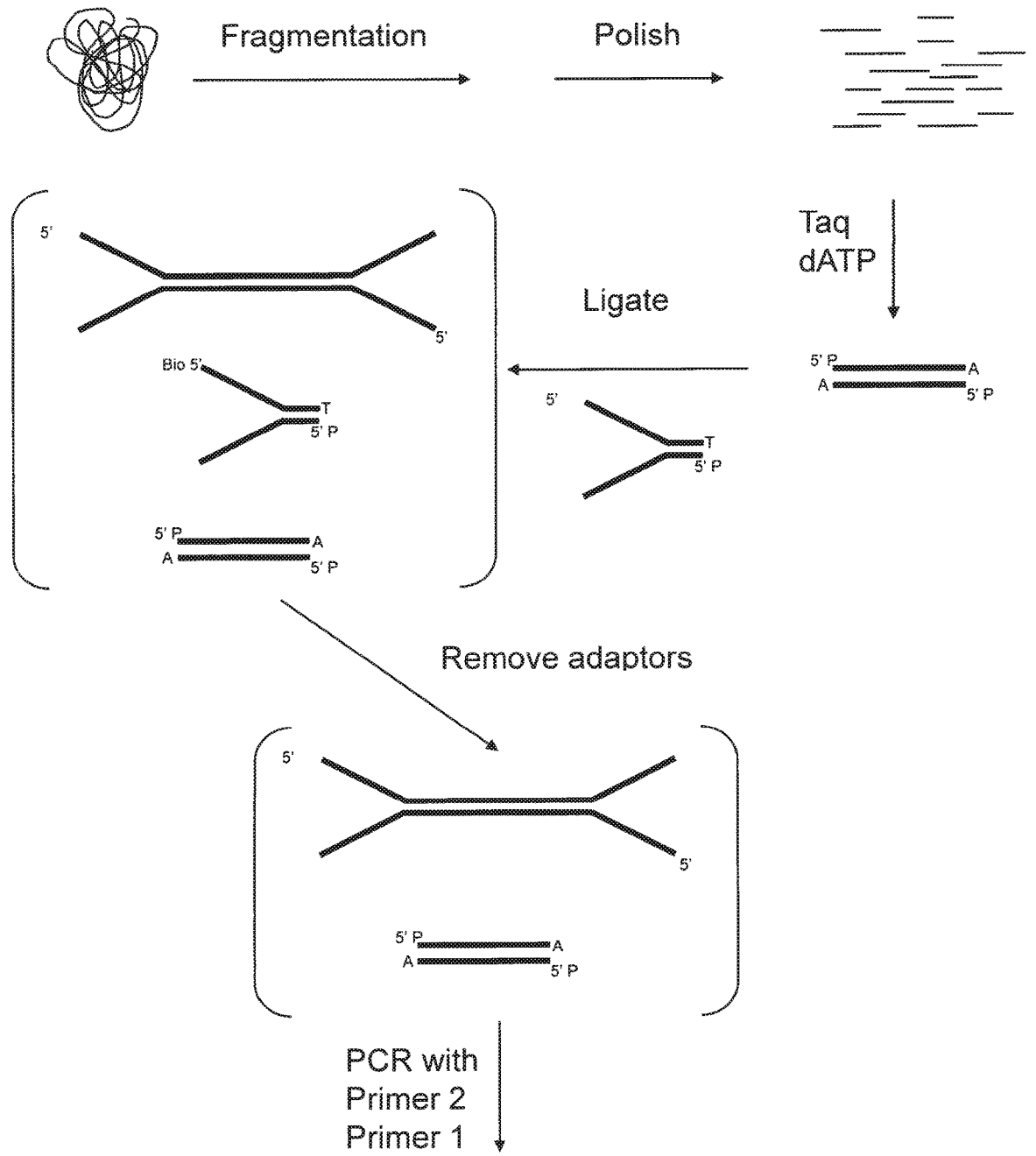

FIG. 5 illustrates an embodiment of the invention, depicting steps of fragmenting a complex sample such as genomic DNA to generate a plurality of target fragments, ligation of the target fragments to mismatch (forked) adaptors to generate adaptor-template constructs and subsequent removal of unbound adaptors, wherein the adaptors do not include a biotin group at the 5' end. The resulting adaptor-target constructs may be subjected to PCR amplification to generate multiple double-stranded copies of each adaptor-target construct. For simplicity, the ligation steps are illustrated for a single adaptor-target construct.

FIGS. 6A-6D illustrate further examples of forked mismatch adaptors for use in the method of the invention, again depicting the permissible blunt or overhang formats at the "ligatable" end of the adaptor. FIG. 6E schematically illustrates the component sequences present in the two strands (denoted Oligo C and Oligo B) which form the adaptor when annealed. Oligo B and Oligo C are prepared with all the cytosine bases in the methylated form. P represents a phosphate group; X and Y represent surface capture functionalities.

Figure 6A:
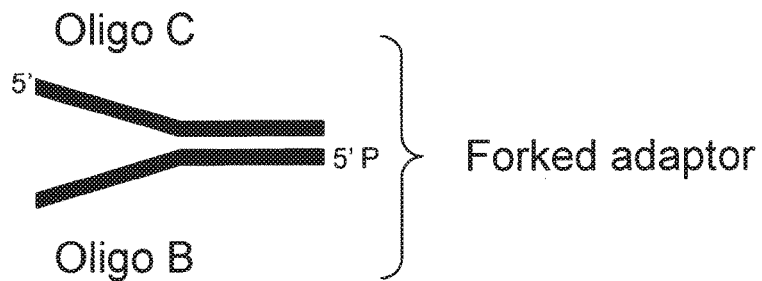
Figure 6B:
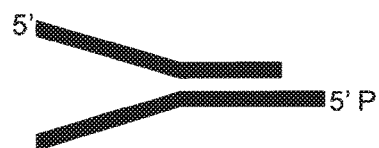
Figure 6C:
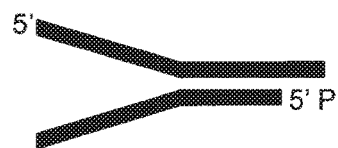
Figure 6D:
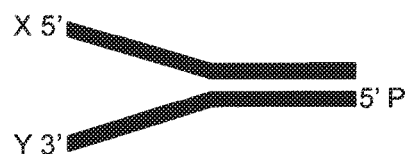
Figure 6E:
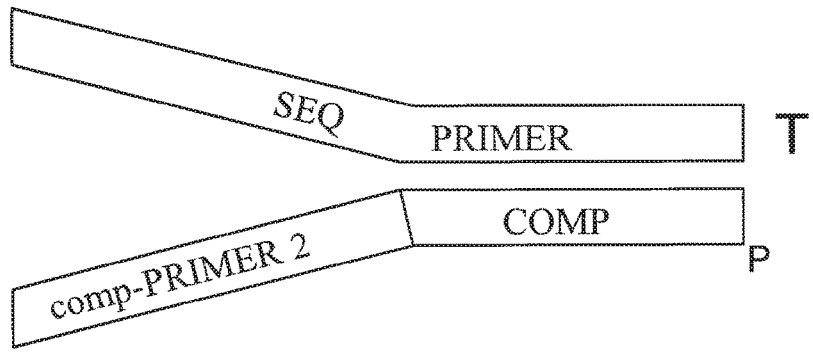
Figure 7A:
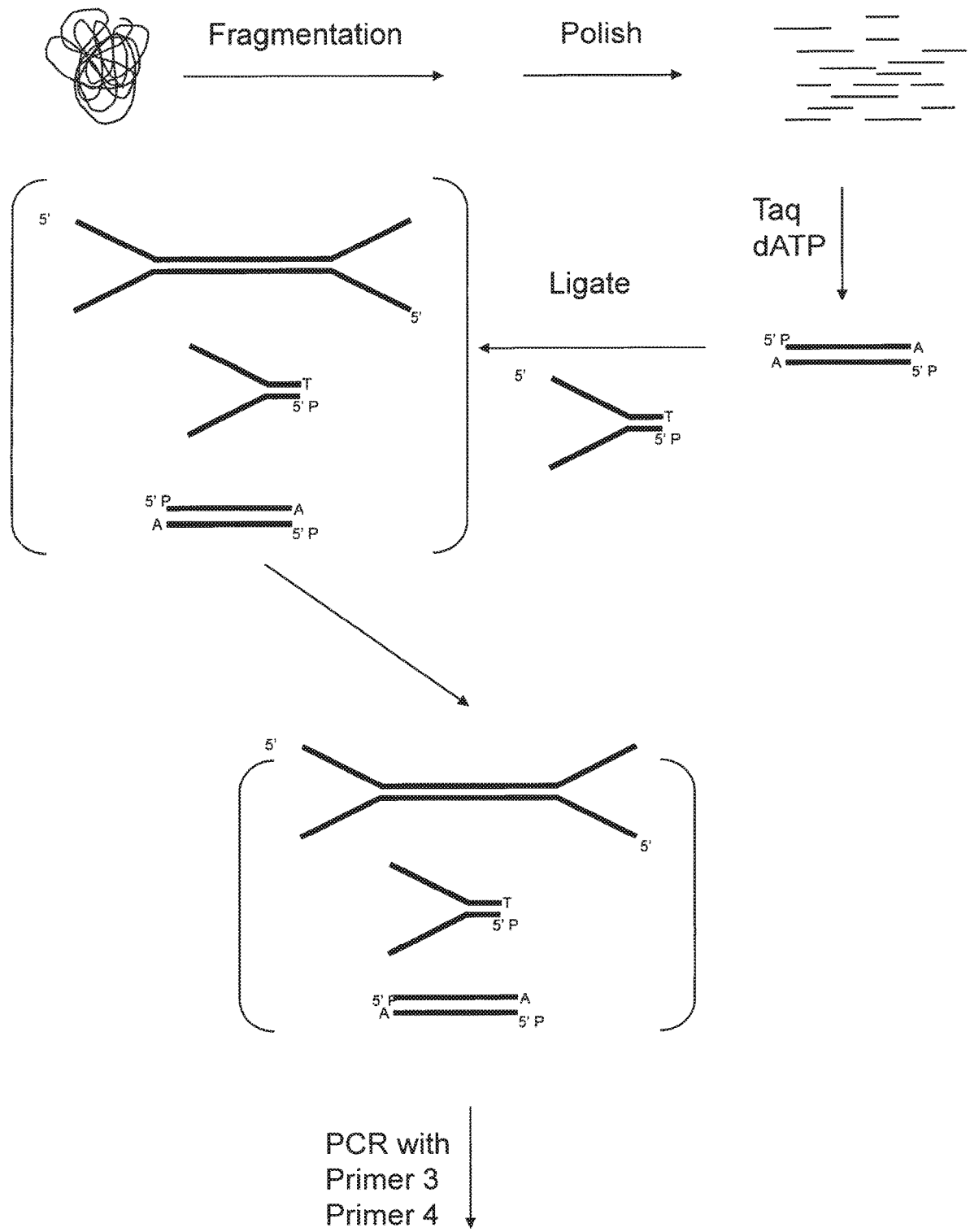
Figure 7B:
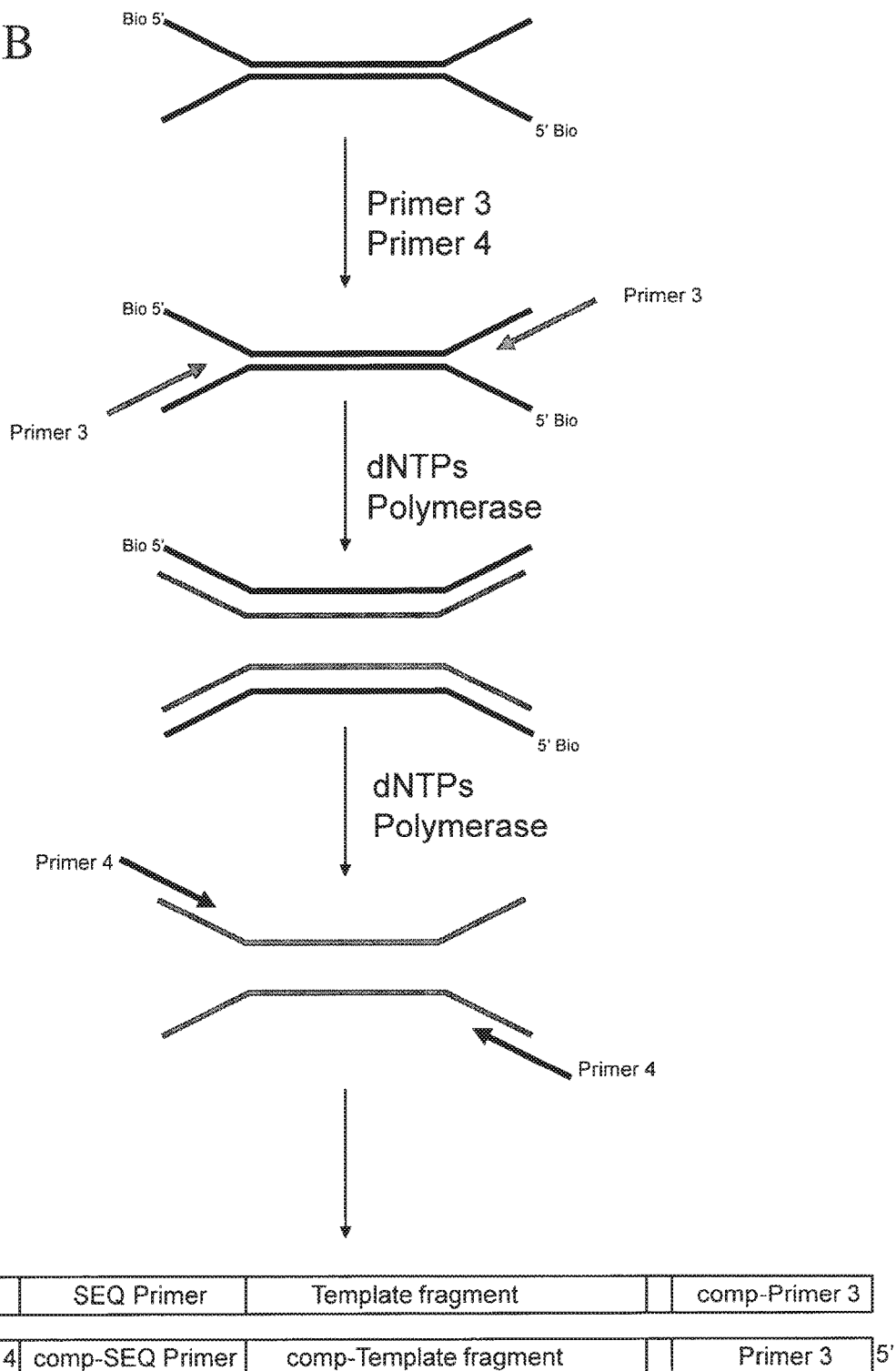

FIGS. 7A and 7B illustrate further embodiments of the invention based on use of the forked adaptors illustrated in FIGS. 6A-6E. FIG. 7A depicts fragmentation and ligation steps substantially similar to those illustrated in FIG. 5. FIG. 7B depicts subsequent PCR amplification using "tailed" PCR primers and schematically illustrates the sequence composition of the double-stranded amplification products formed in the PCR reaction. For simplicity, the ligation and PCR amplification steps are illustrated for a single adaptor-target construct.

FIGS. 8A-8E illustrate alternative embodiments of mismatch adaptors for use in the method of the invention wherein the single stranded region takes the form of a 'bubble'. The oligonucleotides D and E are prepared with the cytosine bases in the methylated form. P represents a phosphate group; X and Y represent surface capture functionalities; W and Z represent modifications to prevent ligation.

Figure 8A:
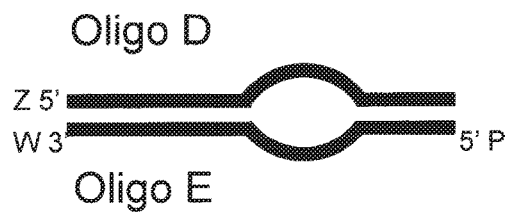
Figure 8B:
Figure 8C:
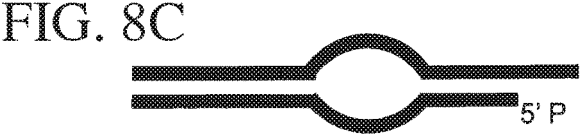
Figure 8D:
Figure 8E:
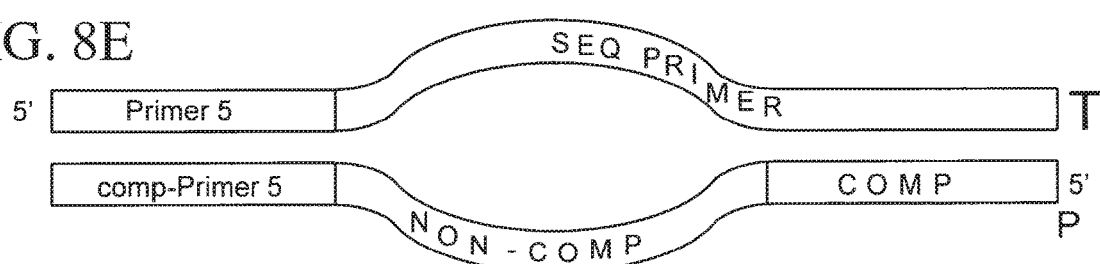
Figure 9A:
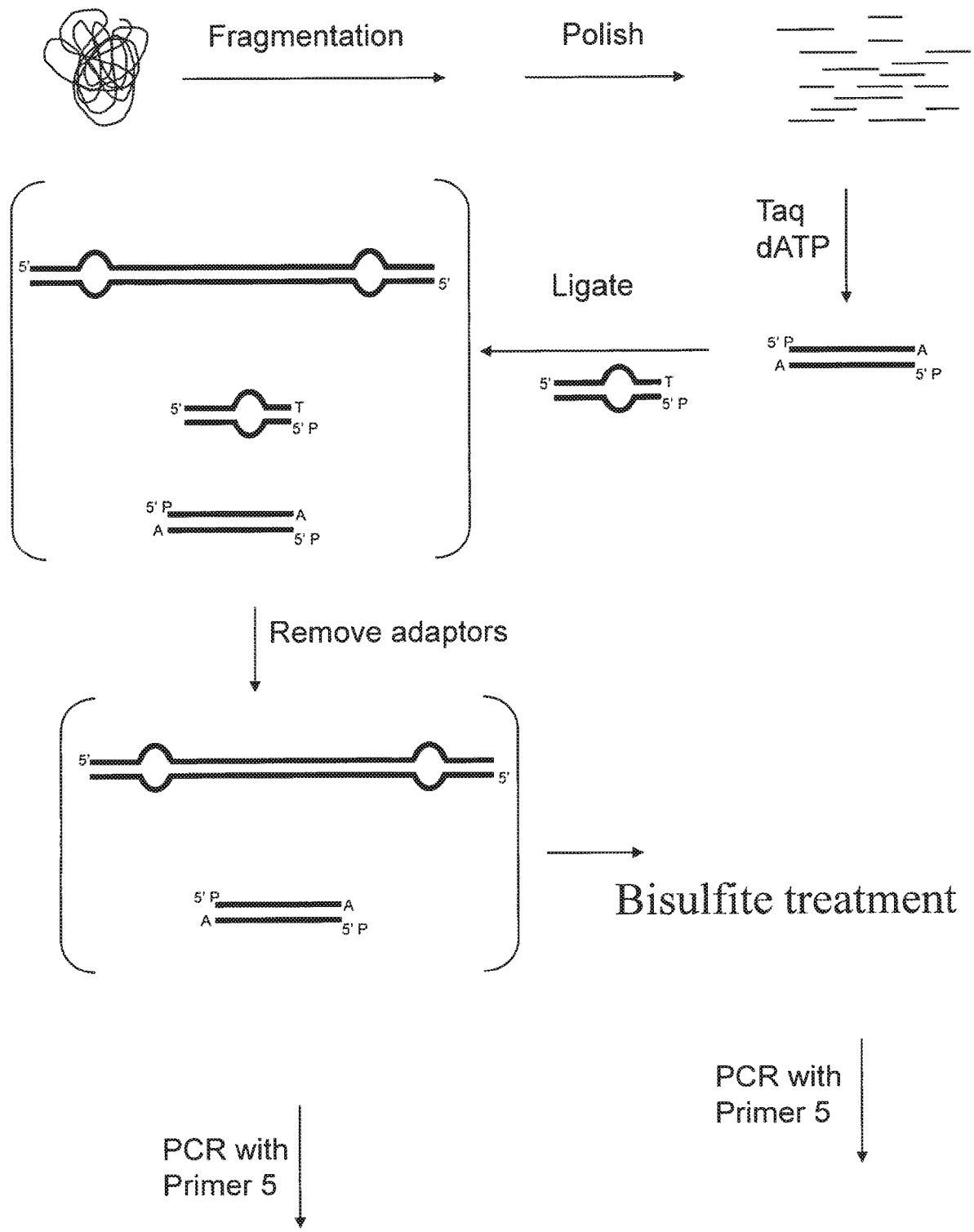
Figure 9B:
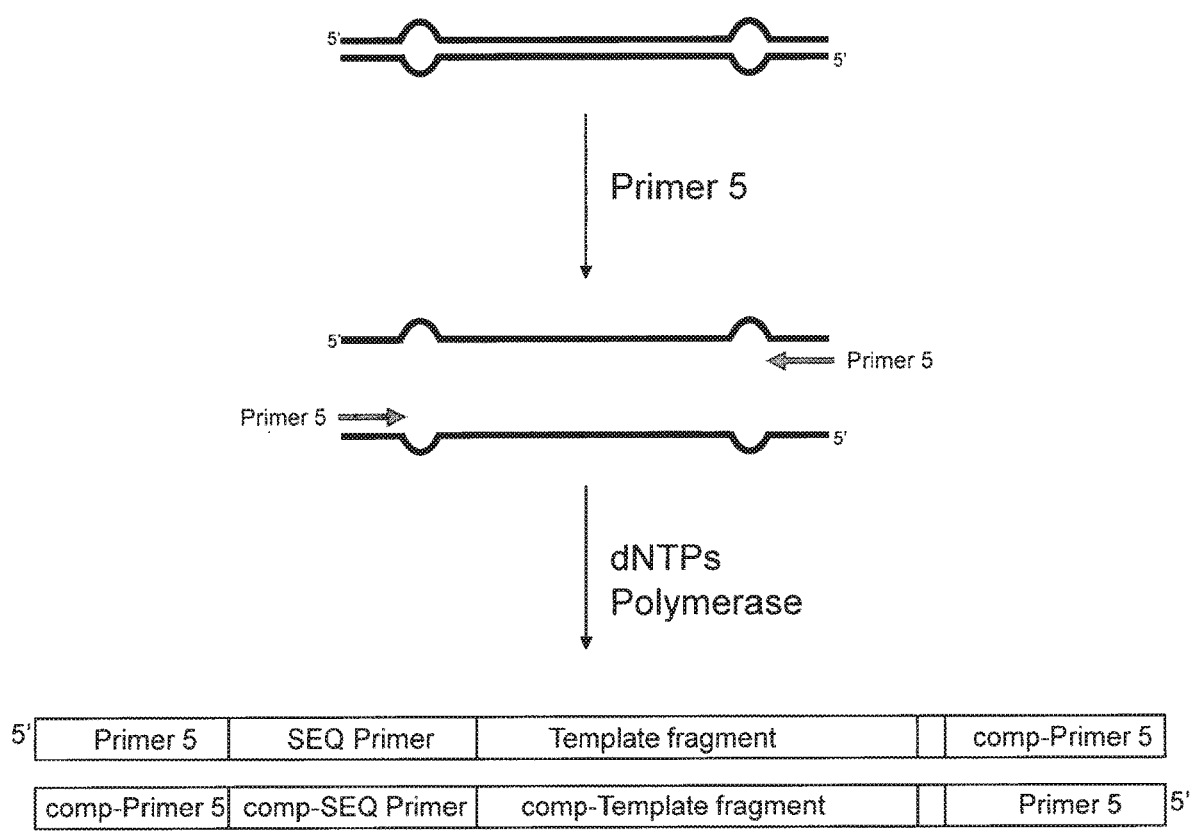

FIGS. 9A and 9B illustrate further embodiments of the invention based on use of the alternative adaptors illustrated in FIGS. 8A-8E. FIG. 9A depicts fragmentation, ligation and subsequent removal of unbound adaptors. FIG. 9B depicts annealing of identical amplification primers to a duplex region of the adaptor on each strand of the adaptor-target construct. The adaptor-target constructs can be amplified by PCR using this single primer species. For simplicity, the ligation steps and primer annealing are illustrated for a single adaptor-target construct.

Figure 10A:
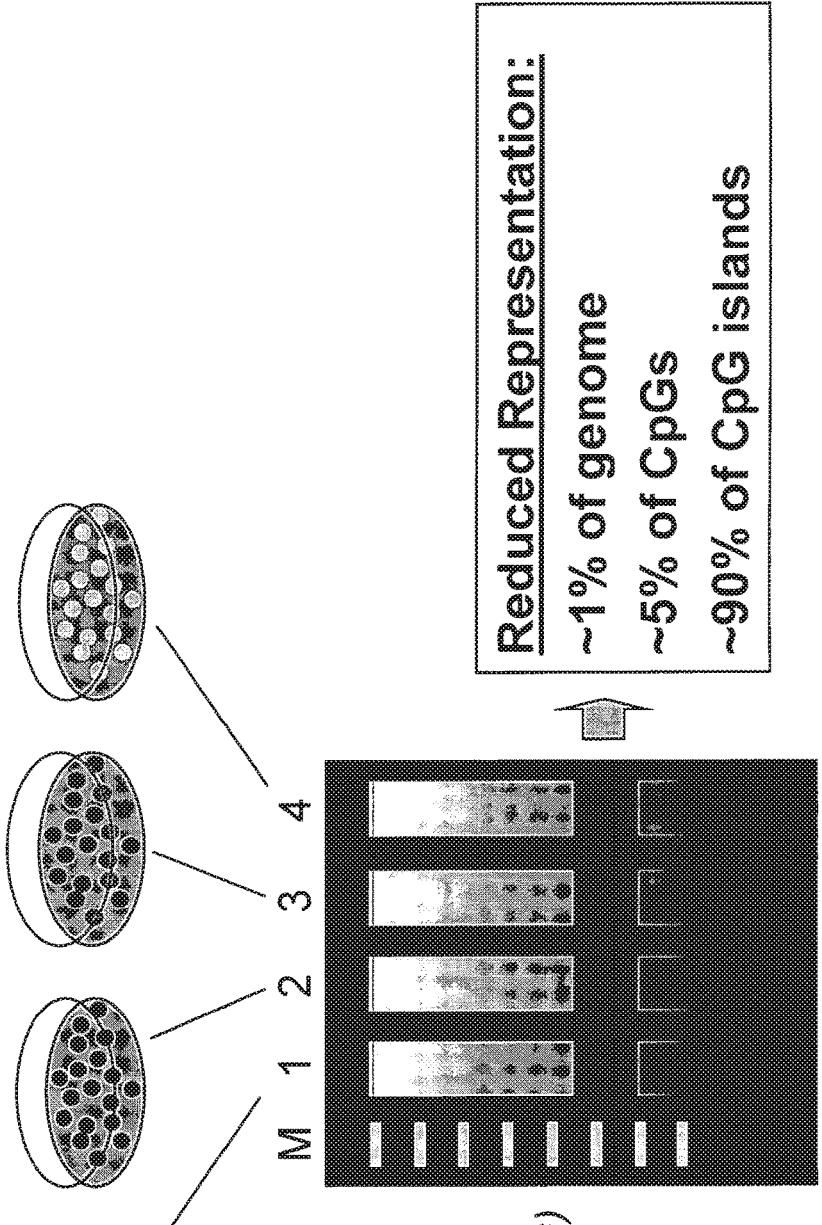
Figure 10B:
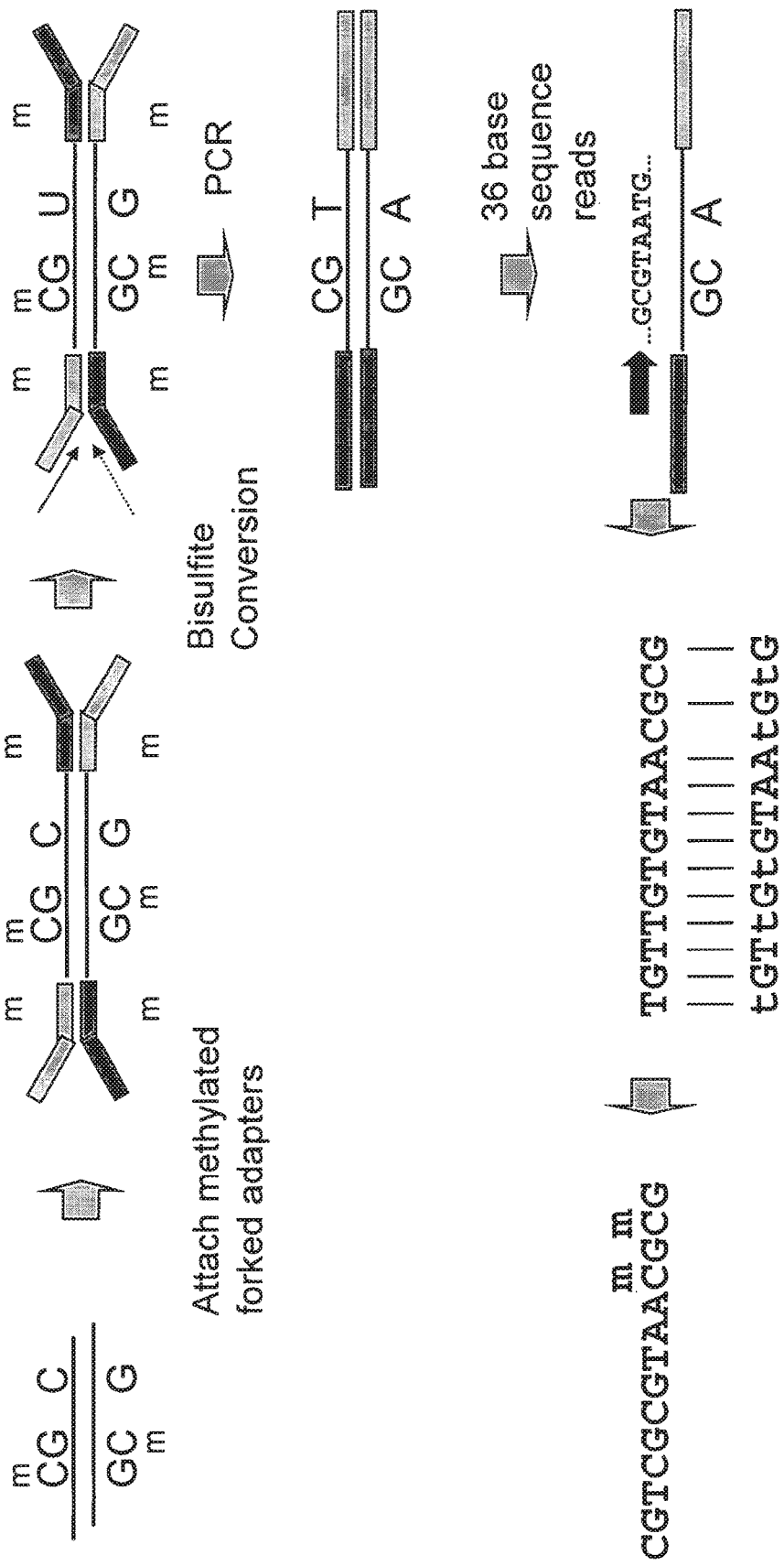
Figure 10C:

FIGS. 10A-10C illustrate an exemplary method of one embodiment of the invention and the data generated thereby. The genomic DNA is fragmented by limit digestion with a methylation-insensitive restriction enzyme rather than by random hydrodynamic shearing. After size fractionation on an agarose gel, a narrow size window is isolated which constitutes only a small portion of the genome. By careful size-selection, essentially the same genomic subfraction can be isolated from different input samples and compared by sequencing. In the exemplary embodiment illustrated in FIG. 10A, genomic DNA from 4 different mouse cell types is digested with the restriction enzyme MspI and size selected to 40-220 bp resulting in a reduced representation of the mouse genome that is enriched for CpG dinucleotides and CpG islands. As shown in FIG. 10B, the size selected fragments are equipped with the methylated forked adapters, bisulfite converted and sequenced as described elsewhere in this document. After mapping the bisulfite sequencing reads by aligning them to the mouse reference genome, methylated cytosines are displayed as bisulfite-resistant Cs. The MspI Reduced Representation Bisulfite Sequencing approach has been used for comparative methylation profiling of four different mouse cell types resulting in redundant coverage of almost one million distinct CpG dinucleotides in each cell type with more than 800,000 CpGs covered in all four cell types (FIG. 10C).

DETAILED DESCRIPTION

In a first aspect, the invention presents a method of analysing the methylation status of cytosine bases in a nucleic acid. The nucleic acid is fragmented, then ligated to universal adaptors wherein all the cytosine bases in the adaptors are methylated at the 5 position of the base. The adaptors comprise two oligonucleotides which are partially complementary such that they can hybridise to form a region of double stranded sequence, but also retain a region of single stranded, non-hybridised sequence. A portion of the adaptor-target construct sample is treated to convert the unmethylated cytosine bases to uracil, and both the treated and untreated portions are sequenced to determine which cytosine bases in the target nucleic acid are methylated.

The ligation of universal adaptors to both ends of the target nucleic acid fragments gives rise to a pool of adaptor-ligated double stranded nucleic acid target fragments with adaptors at both ends of the target. The treatment step to convert the non methylated cytosine bases to uracil is usually performed with sodium bisulfite. After the treatment, the sample can be further amplified to produce a library of template polynucleotide molecules which have common sequences at their 5' and 3' ends. In this context, the term "common" is interpreted as meaning common to all templates in the library, and is a known, artificially introduced exogenous sequence that facilitates amplification of the entire library of template polynucleotide molecules. As explained in further detail below, all templates within the library will contain regions of known, common sequence at (or proximal to) their 5' and 3' ends. The term library therefore refers to the collection of target fragments containing known common sequences at their 3' and 5' ends, and may also be referred to as a 3' and 5' modified library.

The library is formed by ligating identical adaptor polynucleotide molecules ("universal adaptors", the general features of which are defined below) to the 5' and 3' ends of one or more fragmented double stranded nucleic acid target fragments (which may be of known, partially known or unknown sequence) to form adaptor-target constructs and then carrying out an initial primer extension reaction in which extension products complementary to both strands of each individual adaptor-target construct are formed. The resulting primer extension products, and optionally amplified copies thereof, collectively provide a library of template polynucleotides.

The treatment with sodium bisulfite or similar reagent must be performed prior to any amplification steps in order to preserve the methylation status of the original sample. Once the bisulfite treatment has been performed, there is no need for subsequently utilised oligonucleotides to be methylated. In other words, the common sequences in the amplified libraries do not need to be derived from methylated amplification primers. The only sequences that need to be fully methylated are the adaptor sequences that are subjected to the bisulfite treatment.

Each strand of each template molecule in the library formed in the primer extension reaction will therefore have the following structure, when viewed as a single strand:

5'-[common sequence I]-[target sequence]-[common sequence II]-3' wherein "common sequence I" represents a sequence derived from copying a first strand of the universal adaptor and is common to all template molecules in the library generated in the initial primer extension reaction; "target" represents a sequence derived from one strand of the fragmented double stranded nucleic acid target fragments, and may be different in different individual template molecules within the library; and "common sequence II" represents a sequence derived from copying of a second strand of the universal adaptor and is also common to all template molecules in the library generated in the initial primer extension reaction.

Since "common sequence I" and "common sequence II" are common to all template strands in the library they may include "universal" primer-binding sequences, enabling all templates in the library to be ultimately amplified in a solid-phase amplification procedure using universal primers.

It is a key feature of the invention, however, that the common 5' and 3' end sequences denoted "common sequence I" and "common sequence II" are not fully complementary to each other, meaning that each individual template strand can contain different (and non-complementary) universal primer sequences at its 5' and 3' ends.

To determine the methylation status of the nucleic acid, it is generally necessary for libraries of templates to be amplified on a solid support, and ultimately sequenced. Amplified template molecules may therefore include regions of "different" sequence at their 5' and 3' ends, which are nevertheless common to all template molecules in the library. For example, the presence of a common unique sequence at one end only of each template in the library can provide a binding site for a sequencing primer, enabling one strand of each template in the amplified form of the library to be sequenced in a single sequencing reaction using a single type of sequencing primer.

Typically "common sequence I" and "common sequence II" will consist of no more than 100, or no more than 50, or no more than 40 consecutive nucleotides at the 5' and 3' ends, respectively, of each strand of each template polynucleotide. The precise length of the two sequences may or may not be identical. The nucleotide sequences of "common sequence I" and "common sequence II" in the template polynucleotides will be determined in part by the sequences of the adaptor strands ligated to the target polynucleotides and in part by the sequence of the primer used in the initial primer extension reaction, and any subsequent rounds of nucleic acid amplification.

Additional sequences may be included at the 5' end of "common sequence II" in the amplified products, for example, by the use of "tailed" PCR primers. In embodiments where the amplification is performed using a "tailed" amplification primer that extends beyond the 5' end of the adaptor sequence, then the products of the amplification reaction will be double-stranded polynucleotides, one strand of which has the structure:

5'-[common sequence I]-[target sequence]-[common sequence II]-3'

It will be appreciated that "common sequence II" in the amplification products may differ somewhat to the "common sequence II" present in the products of the primer extension using the shorter primers, since the former will be determined solely by the sequence of the ligated adaptor, whereas the latter will be determined by both the adaptor sequence plus the overhanging sequence of the amplification primers that can be copied during the amplification cycles. Nevertheless, since the PCR primer is designed to anneal to a sequence in the initial extension products which is complementary to the 3' adaptor, the two forms of "common sequence II" will contain identical sequences at the 3' end.

The precise nucleotide sequences of the common regions of the template molecules in the library are generally not material to the invention and may be selected by the user. The common sequences must at least comprise "primer-binding" sequences which enable specific annealing of amplification primers when the templates are in use in a solid-phase amplification reaction. The primer-binding sequences are thus determined by the sequence of the primers ultimately used for solid-phase amplification. The sequence of these primers, in turn, is advantageously selected to avoid or minimise binding of the primers to the target portions of the templates within the library under the conditions of the amplification reaction, but is otherwise not particularly limited. By way of example, if the target portions of the templates are derived from human genomic DNA, then the sequences of the primers used in solid phase amplification should ideally be selected to minimise non-specific binding to any human genomic sequence.

The universal adaptor polynucleotides used in the method of the invention must contain a region of both double and single stranded sequence, i.e. they must not be formed by annealing of fully complementary polynucleotide strands. Such adaptors are defined as 'mismatched' or 'mismatch' adaptors as long as they contain at least one strand that is single stranded.

Mismatch adaptors for use in the invention can be formed by annealing two partially complementary polynucleotide strands so as to provide, when the two strands are annealed, at least one duplex region and at least one single stranded region. The single stranded region in said adaptors is defined as the "mismatch" region.

The "duplex region" of the adaptor is a short double-stranded region, typically comprising 5 or more consecutive base pairs, formed by annealing of the two partially complementary polynucleotide strands.

Generally it is advantageous for the duplex region to be as short as possible without loss of function. By "function" in this context is meant that the duplex region forms a stable duplex under standard reaction conditions for an enzyme-catalysed nucleic acid ligation reaction, which are known to the skilled reader (e.g. incubation at a temperature in the range of from 4° C. to 25° C. in a ligation buffer appropriate for the enzyme), such that the two strands forming the adaptor remain partially annealed during ligation of the adaptor to a target molecule. It is not absolutely necessary for the duplex region to be stable under the conditions typically used in the annealing steps of primer extension or PCR reactions.

Since identical adaptors are ligated to both ends of each fragmented double stranded nucleic acid target fragment, the target sequence in each adaptor-target construct will be flanked by complementary sequences derived from the duplex region of the adaptors. The longer the duplex region, and hence the complementary sequences derived therefrom in the adaptor-target constructs, the greater the possibility that the adaptor-target construct is able to fold back and base-pair to itself in these regions of internal self-complementarity under the annealing conditions used in primer extension and/or PCR. Generally it is preferred for the duplex region to be 20 or fewer, 15 or fewer, or 10 or fewer base pairs in length in order to reduce this effect. The stability of the duplex region may be increased, and its length potentially reduced, by the inclusion of non-natural nucleotides which exhibit stronger base-pairing than standard Watson-Crick base pairs.

In a particular embodiment, the two strands of the adaptor are 100% complementary in the duplex region. It will be appreciated, however, that one or more mismatched nucleotides may be tolerated within the duplex region, provided that the two strands are capable of forming a stable duplex under standard ligation conditions.

Adaptors for use in the invention will generally include a duplex region adjacent to the "ligatable" end of the adaptor, i.e. the end that is joined to a target polynucleotide in the ligation reaction. The ligatable end of the adaptor may be blunt or, in other embodiments, short 5' or 3' overhangs of one or more nucleotides may be present to facilitate/promote ligation. The 5' terminal nucleotide at the ligatable end of the adaptor should be phosphorylated to enable phosphodiester linkage to a 3' hydroxyl group on the target polynucleotide.

The term "mismatch region" refers to a region of the adaptor wherein the sequences of the two polynucleotide strands forming the adaptor exhibit a degree of non-complementarity such that the two strands are not capable of annealing to each other under standard annealing conditions for a primer extension or PCR reaction. The two strands in the mismatch region may exhibit some degree of annealing under standard reaction conditions for an enzyme-catalysed ligation reaction, provided that the two strands revert to single stranded form under annealing conditions.

The conditions encountered during the annealing steps of a PCR reaction are generally known to one skilled in the art, although the precise annealing conditions will vary from reaction to reaction (see Sambrook et al., 2001, *Molecular Cloning, A Laboratory Manual*, 3rd Ed, Cold Spring Harbor Laboratory Press, Cold Spring Harbor Laboratory Press, NY; Current Protocols, eds Ausubel et al.). Typically, such conditions may comprise, but are not limited to, (following a denaturing step at a temperature of about 94° C. for about one minute) exposure to a temperature in the range of 50° C. to 65° C. (preferably 55-58° C.) for a period of about 1 minute in standard PCR reaction buffer, (optionally supplemented with 1M betaine and 1.3% DMSO). Different annealing conditions may be used for a single primer extension reaction not forming part of a PCR reaction (again see Sambrook et al., 2001, *Molecular Cloning, A Laboratory Manual*, 3rd Ed, Cold Spring Harbor Laboratory Press, Cold Spring Harbor Laboratory Press, NY; Current Protocols, eds Ausubel et al.).

It is to be understood that the 'mismatch region' is provided by different portions of the same two polynucleotide strands which form the double-stranded region(s). Mismatches in the adaptor construct can take the form of one strand being longer than the other, such that there is a single stranded region on one of the strands, or a sequence selected such that the two strands do not hybridise, and thus form a single stranded region on both strands. Adaptors used in this particular example are termed 'forked adaptors'. The mismatches may also take the form of 'bubbles', wherein both ends of the adaptor construct(s) are capable of hybridising to each other and forming a duplex, but the central region is not. The portion of the strand(s) forming the mismatch region does not anneal under conditions in which other portions of the same two strands are annealed to form one or more double-stranded regions. For avoidance of doubt, it is to be understood that a single-stranded or single base overhang at the 3' end of a polynucleotide duplex that subsequently undergoes ligation to the target sequences does not constitute an 'mismatch region' in the context of this invention.

The portions of the two strands forming the mismatch region typically comprise at least 10, or at least 15, or at least 20 consecutive nucleotides on each strand. The lower limit on the length of the mismatch region will typically be determined by function, for example, the need to provide a suitable sequence for binding of a primer for primer extension, PCR and/or sequencing. Theoretically there is no upper limit on the length of the mismatch region, except that in general it is advantageous to minimise the overall length of the adaptor, for example, in order to facilitate separation of unbound adaptors from adaptor-target constructs following the ligation step. Therefore, it is preferred that the mismatch region should be fewer than 50, or fewer than 40, or fewer than 30, or fewer than 25 consecutive nucleotides in length on each strand.

The portions of the two forked adaptor strands forming the mismatch region should preferably be of similar length, although this is not absolutely essential, provided that the length of each portion is sufficient to fulfil its desired function (e.g. primer binding).

In a particular embodiment, the portions of the two forked adaptor strands forming the mismatch region will be completely mismatched, or 100% non-complementary. However, skilled readers will be appreciate that some sequence "matches", i.e. a lesser degree of non-complementarity may be tolerated in this region without affecting function to a material extent. As aforesaid, the extent of sequence mismatching or non-complementarity must be such that the two strands in the mismatch region remain in single-stranded form under annealing conditions as defined above.

The precise nucleotide sequence of the adaptors is generally not material to the invention and may be selected by the user such that the desired sequence elements are ultimately included in the common sequences of the library of templates derived from the adaptors, for example, to provide binding sites for particular sets of universal amplification primers and/or sequencing primers. Additional sequence elements may be included, for example, to provide binding sites for sequencing primers which will ultimately be used in sequencing of template molecules in the library, or products derived from solid-phase amplification of the template library. The adaptors, or amplification primers may further include "tag" sequences, which can be used to tag or mark template molecules derived from a particular source. The general features and use of such tag sequences is described in applicant's pending application published as WO 05/068656, the contents of which are incorporated herein by reference in its entirety.

Although the precise nucleotide sequence of the methylated adaptor is generally non-limiting to the invention, the sequences of the individual strands in the mismatch region of the forked adaptors should be such that neither individual strand exhibits any internal self-complementarity which could lead to self-annealing, formation of hairpin structures, etc. under standard annealing conditions. Self-annealing of a strand in the mismatch region is to be avoided as it may prevent or reduce specific binding of an amplification primer to this strand.

The universal adaptors are preferably formed from two strands of DNA, but may include mixtures of natural and non-natural nucleotides (e.g. one or more ribonucleotides)

linked by a mixture of phosphodiester and non-phosphodiester backbone linkages. Other non-nucleotide modifications may be included such as, for example, biotin moieties, blocking groups and capture moieties for attachment to a solid surface, as discussed in further detail below. The biotin moieties may be used to effect isolation and removal of any unligated target fragments from the ligation reaction.

The one or more "target polynucleotide duplexes" to which the adaptors are ligated may be any polynucleotide molecules that it is desired to amplify by solid-phase PCR, generally with a view to sequencing. The target polynucleotide duplexes may originate in double-stranded DNA form (e.g. genomic DNA fragments) or may have originated in single-stranded form, as DNA or RNA. The sample can not have been copied by a polymerase prior to analysis, otherwise the methylation status of the sample will not be maintained. Any bisulfite treatment must be carried out on the original sample prior to any copying or amplification steps such as reverse transcription or PCR amplification. The precise sequence or source of the target molecules is generally not material to the invention, and may be known or unknown, and the methodology described herein is applicable to the methylation analysis of the genome of any biological organism.

The method of the invention may be applied to multiple copies of the same target molecule (so-called monotemplate applications) or to a mixture of different target molecules which differ from each other with respect to nucleotide sequence over all or a part of their length. The method may be applied to a plurality of target molecules derived from a common source, for example, a library of genomic DNA fragments derived from a particular individual or organism. In one embodiment, the target polynucleotides comprise fragments of genomic DNA, which may be human. The fragments may be derived from a whole genome or from part of a genome (e.g. a single chromosome or sub-fraction thereof), and from one individual or several individuals. Techniques for fragmentation of genomic DNA, for example, by chemical or enzymatic digestion or mechanical shearing, sonication or nebulisation are encompassed by the present invention. The fragmentation may be random, for example using hydro-dynamic shearing or nebulisation such that the ends of the fragments have random sequences. Alternatively the nucleic acid sample may be treated with an enzyme such as a restriction endonuclease such that the ends of the fragments all comprise the same sequence. The enzyme may recognise certain sequences for example those contain high levels of C and G bases. The enzyme may select for CpG dinucleotides or CpG islands, for example MspI, whose recognition site is 5'-CCGG-3' and cuts to give a 3'GC overhang on each fragment.

"Ligation" of adaptors to the 5' and 3' ends of each fragmented double stranded nucleic acid target fragment involves joining of the two polynucleotide strands of the adaptor to the double-stranded target polynucleotide such that covalent linkages are formed between both strands of the two double-stranded molecules. Preferably such covalent linking takes place by formation of a phosphodiester linkage between the two polynucleotide strands but other means of covalent linkage (e.g. non-phosphodiester backbone linkages) may be used. However, it is an essential requirement that the covalent linkages formed in the ligation reactions allow for read-through of a polymerase, such that the resultant construct can be copied in a primer extension reaction using primers which bind to sequences in the regions of the adaptor-target construct that are derived from the adaptor molecules.

The ligation reactions will preferably be enzyme-catalysed. The nature of the ligase enzyme used for enzymatic ligation is not particularly limited. Non-enzymatic ligation techniques (e.g. chemical ligation) may also be used, provided that the non-enzymatic ligation leads to the formation of a covalent linkage which allows read-through of a polymerase, such that the resultant construct can be copied in a primer extension reaction.

The desired products of the ligation reaction are adaptor-target constructs in which universal, methylated adaptors are ligated at both ends of each target polynucleotide, given the structure adaptor-target-adaptor. Conditions of the ligation reaction should therefore be optimised to maximise the formation of this product, in preference to targets having an adaptor at one end only.

The products of the ligation reaction may be subjected to purification steps in order to remove unbound adaptor molecules before the adaptor-target constructs are processed further. Any suitable technique may be used to remove excess unbound adaptors, particular examples of which will be described in further detail below.

Following bisulfite treatment, adaptor-target constructs formed in the ligation reaction may be subjected to an amplification reaction in which a primer oligonucleotide is annealed to an adaptor portion of each of the adaptor-target constructs and extended by sequential addition of nucleotides to the free 3' hydroxyl end of the primer to form extension products complementary to at least one strand of each of the adaptor-target constructs.

The primers used for the amplification reaction will be capable of annealing to each individual strand of adaptor-target constructs having adaptors ligated at both ends, and can be extended so as to obtain two separate primer extension products, one complementary to each strand of the construct. Thus, in a particular embodiment, the initial primer extension reaction results in formation of primer extension products complementary to each strand of each adaptor-target In a particular embodiment, the primer used in the initial primer extension reaction anneals to a primer-binding sequence (in one strand) in the mismatch region of the adaptor. The primer may also hybridise to the double stranded region of the adaptor. If the adaptor contains a 3'-overhanging base complementary to an overhanging base in the target sequence, then the amplification primers may also hybridise to the ligated target region of the fragmented double stranded nucleic acid target fragments. Such amplification primers may be beneficial in helping to reduce the amplification of any adaptor dimers which may contaminate the sample preparation.

The term "annealing" as used in this context refers to sequence-specific binding/hybridisation of the primer to a primer-binding sequence in an adaptor region of the adaptor-target construct under the conditions used for the primer annealing step of the initial primer extension reaction.

The products of the primer extension reaction may be subjected to standard denaturing conditions in order to separate the extension products from strands of the adaptor-target constructs. Optionally the strands of the adaptor-target constructs may be removed at this stage if, for example, the adaptors contain a biotin sequence that can be selectively bound using an avidin or streptavidin bead. The extension products (with or without the original strands of the adaptor-target constructs) collectively form a library of template polynucleotides which can be used as templates for solid-phase PCR.

If desired, only a single amplification primer can be added to the amplification mixture, and the initial primer extension reaction may be repeated one or more times, through rounds of primer annealing, extension and denaturation, in order to form multiple copies of the same extension products complementary to the adaptor-target constructs.

In other embodiments the initial extension products may be amplified by conventional solution-phase PCR, as described in further detail below. In a particular embodiment, both primers used for PCR amplification anneal to different primer-binding sequences on opposite strands in the mismatch region of the forked adaptor. Other embodiments may, however, be based on the use of a single type of amplification primer which anneals to a primer-binding sequence in the duplex region of the adaptor. The amplification conditions also allow for amplification with more than two primers if desired to carry out nested PCR and control the length of the sequences added to the target fragments.

Inclusion of the initial primer extension step, and optionally further rounds of PCR amplification, to form complementary copies of the adaptor-target constructs prior to solid-phase PCR is advantageous, for several reasons. Firstly, inclusion of the primer extension step, and subsequent PCR amplification, acts as an enrichment step to select for adaptor-target constructs with adaptors ligated at both ends. Only target constructs with adaptors ligated at both ends provide effective templates for solid-phase PCR using common or universal primers specific for primer-binding sequences in the adaptors, hence it is advantageous to produce a template library comprising only double-ligated targets prior to solid-phase ligation.

Secondly, inclusion of the initial primer extension step, and subsequent PCR amplification, permits the length of the common sequences at the 5' and 3' ends of the target to be increased prior to solid-phase PCR. As outlined above, it is generally advantageous for the length of the adaptor molecules to be kept as short as possible, to maximise the efficiency of ligation and subsequent removal of unbound adaptors. However, for the purposes of solid-phase PCR it may be an advantage to have longer sequences of common or "universal" sequences at the 5' and 3' ends of the templates to be amplified. Inclusion of the primer extension (and subsequent amplification) steps means that the length of the common, known sequences at one (or both) ends of the polynucleotides in the template library can be increased after ligation by inclusion of additional sequences at the 5' ends of the primers used for primer extension (and subsequent amplification). The use of such "tailed" primers is described in further detail below.

Various non-limiting specific embodiments of the method of the invention are described in further detail with reference to the accompanying drawings. Features described as being preferred in relation to one specific embodiment of the invention apply mutatis mutandis to other specific embodiments of the invention unless stated otherwise.

FIGS. 1A-1E illustrate several embodiments of a particular type of mismatch adaptor for use in the method of the invention. The adaptor is formed by annealing two single-stranded oligonucleotides, herein referred to as "oligo A" and "oligo B". Oligo A and oligo B may be prepared by conventional automated oligonucleotide synthesis techniques in routine use in the art. The cytosine bases in oligonucleotides A and B must be methylated at the 5 position of the base. Such oligonucleotides can be prepared according to standard procedures, from phosphoramidites in which the cytosine base is methylated. The oligonucleotides are partially complementary such that the 3' end of oligo A is complementary to the 5' end of oligo B. The 5' end of oligo A and the 3' end of oligo B are not complementary to each other. When the two strands are annealed, the resulting structure is double stranded at one end (the duplex region) and single stranded at the other end (the mismatch region) and is referred to herein as a "forked adaptor" (FIG. 1A). The duplex region of the forked adaptor may be blunt-ended (FIG. 1B) or it may have an overhang. In the latter case, the overhang may be a 3' overhang (FIG. 1C) or a 5' overhang (FIG. 1D), and may comprise a single nucleotide or more than one nucleotide.

The 5' end of the double-stranded part of the forked adaptor is phosphorylated, i.e. the 5' end of oligo B (FIGS. 1A-1D). The presence of the 5' phosphate group identifies this as the "ligatable" end of the adaptor. The 5' end of oligo A may be biotinylated or bear another functionality (represented by X) that enables it to be captured on a surface, such as a bead. Alternative functionalities other than biotin are known to those skilled in the art. The 3' end of oligo B may also be biotinylated or bear another functionality (represented by Y) that enables it to be captured on a surface (FIG. 1D).

The phosphodiester bonds that comprise the back-bone of the oligonucleotides may be replaced with non-enzymatically cleavable bonds such as phosphorothioate bonds. Preferably only the last, or last and penultimate, phosphodiester bonds at both the 3' and 5' ends of the oligonucleotides will be substituted with phosphorothioate bonds. In a particular embodiment of the invention, oligo A contains a biotin group on its 5' end, oligo B is phosphorylated at its 5' end and the double-stranded portion of the duplex contains a single base 3' overhang comprising a 'T' nucleotide. Oligo A consists of two regions: a region at the 5' end which is identical to a region of an amplification primer to be used for PCR amplification, referred to herein as "PRIMER 1" sequence, and at its 3' end a region identical to that of a universal sequencing primer, referred to herein as "SEQ PRIMER" sequence, plus an additional 'T' nucleotide on the 3' end. Oligo B also consists of two regions: a region at its 5' end that is complementary to only part of the 3' end of the SEQ PRIMER sequence in Oligo A, excluding the 'T' overhang of Oligo A, and a region complementary to that of a universal PCR amplification primer, herein referred to as "comp-PRIMER 2" at its 3' end (FIG. 1E).

Figure 2A:
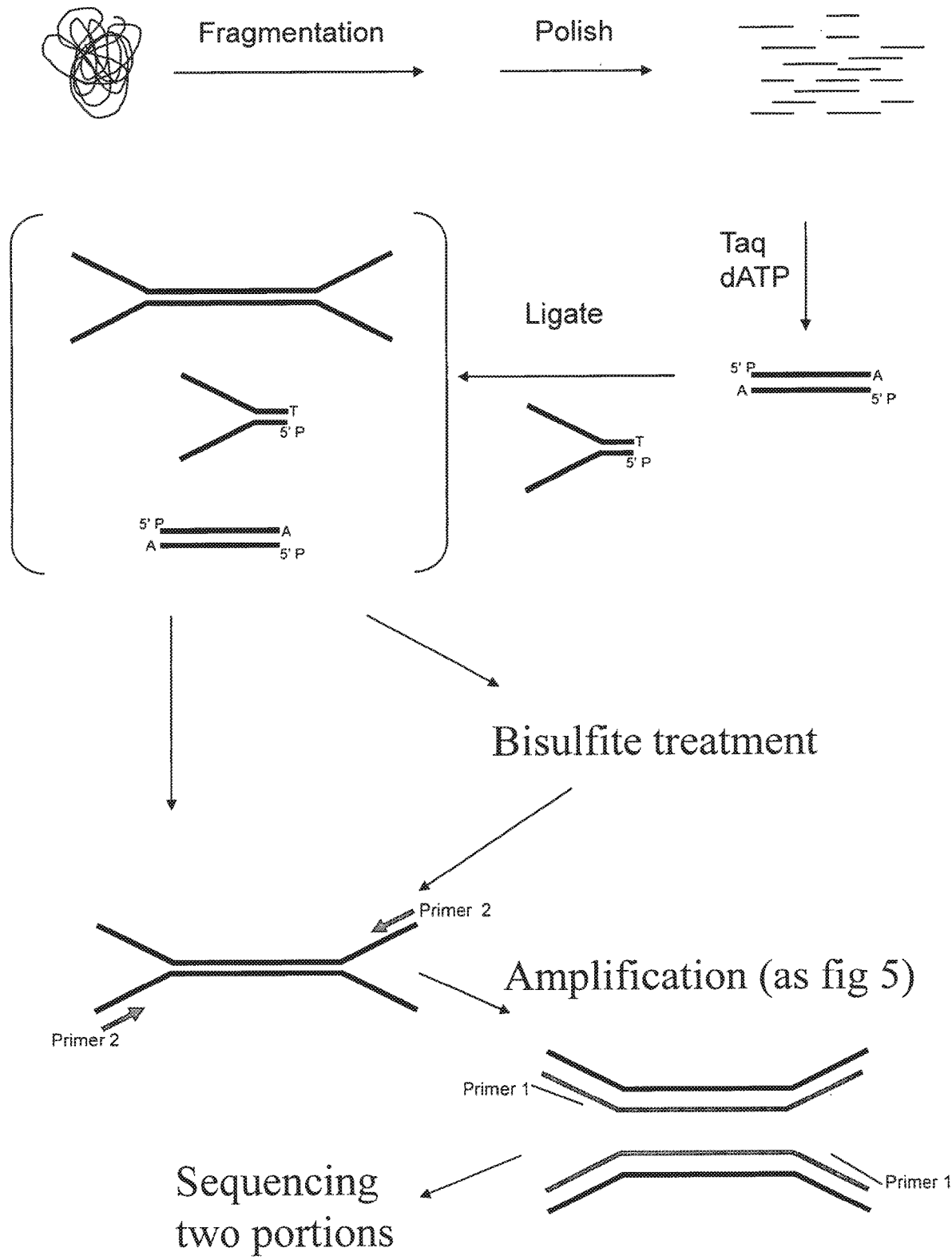

FIG. 2A illustrates one embodiment of the method of the invention based on use of the forked adaptors illustrated in FIGS. 1A-1E. A mixture of target DNA molecules of different sequence may be prepared by mixing a number, greater than one, of individual DNA molecules. In an aspect of the invention, genomic DNA is fragmented into small molecules, less than 1000 base pairs, more particularly less than 500 base pairs, and most particularly between 100-200 base pairs. Fragmentation of DNA may be achieved by a number of methods including: enzymatic digestion, chemical cleavage, sonication, nebulisation, or hydroshearing, preferably nebulisation.

Fragmented DNA may be rendered blunt-ended by a number of methods known to those skilled in the art. In a particular method, the ends of the fragmented DNA are "polished" with T4 DNA polymerase and Klenow polymerase, a procedure well known to skilled practitioners, and then phosphorylated with a polynucleotide kinase enzyme. A single 'A' deoxynucleotide is then added to both 3' ends of the DNA molecules using Taq polymerase or Klenow exo minus polymerase enzyme, producing a one-base 3' overhang that is complementary to the one-base 3' overhang on the double-stranded end of the forked adaptor.

A ligation reaction between the forked adaptor and the DNA fragments is then performed using a suitable ligase enzyme (e.g. T4 DNA ligase) which joins two copies of the adaptor to each DNA fragment, one at either end, to form adaptor-target constructs. The products of this reaction can be treated immediately with sodium bisulfite before any further purification or amplification steps. The ligated sample may be split such that the treated and untreated portions can be compared, although if a reference sequence is known, then the whole sample or a portion thereof can be treated, sequenced and compared against the reference without the need to sequence an untreated version of the sample. The analysis of the nucleic acid sequences can be performed either by comparing against the know reference or against a treated sample for the purpose of determining which cytosine bases have been converted to uracil bases due to the treatment step. The bisulfite treated sample is further treated to remove the sodium bisulfite to prevent contamination of the untreated or untreated amplified sample. Both portions may be combined after bisulfite treatment and work-up, or separate amplification steps may be performed.

An oligonucleotide, herein referred to as PRIMER 2, which hybridises to the "comp-PRIMER 2" sequence on the oligo B strand of the adaptor-target constructs can be used in an initial primer extension reaction to generate a complementary copy of the adaptor-target strand. An oligonucleotide, herein referred to as PRIMER 1, which hybridises to the sequence produced by extension of primer 2, can be used to enable a standard two primer amplification reaction. The library produced by the amplification reaction can be used directly, or further purified, for use in sequencing to determine the differences between the treated and untreated samples.

Figure 2B:
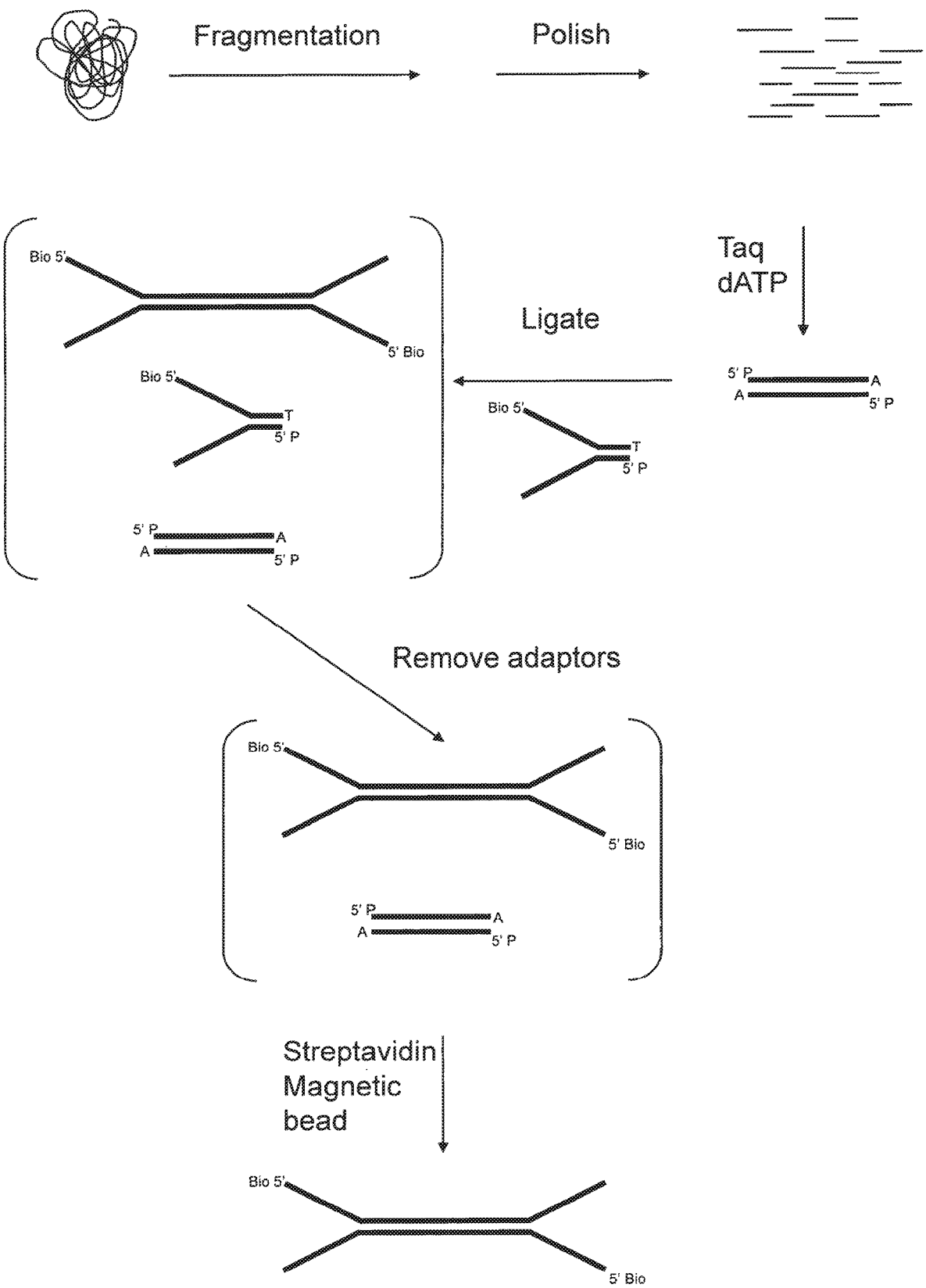

FIG. 2B shows a ligation reaction between a biotinylated forked adaptor and the DNA fragments performed using a suitable ligase enzyme (e.g. T4 DNA ligase) which joins two copies of the adaptor to each DNA fragment, one at either end, to form adaptor-target constructs. The products of this reaction can be purified from unligated adaptor by a number of means, including size-inclusion chromatography, preferably by electrophoresis through an agarose gel slab followed by excision of a portion of the agarose that contains the DNA greater in size than the size of the adaptor.

After the excess adaptor has been removed, unligated target DNA remains in addition to ligated adaptor-target constructs and this can be removed by selectively capturing only those target DNA molecules that have adaptor attached. The presence of a biotin group on the 5' end of Oligo A of the adaptor enables any target DNA ligated to the adaptor to be captured on a surface coated with streptavidin, a protein that selectively and tightly binds biotin. Streptavidin can be coated onto a surface by means known to those skilled in the art. In a particular method, commercially available magnetic beads that are coated in streptavidin can be used to capture ligated adaptor-target constructs. The application of a magnet to the side of a tube containing these beads immobilises them such that they can be washed free of the unligated target DNA molecules (FIG. 2B). If desired, the bisulfite treatment can be performed on the immobilised sample, to allow the bisulfite to be easily removed from the treated adaptor-target constructs.

Figure 2C:
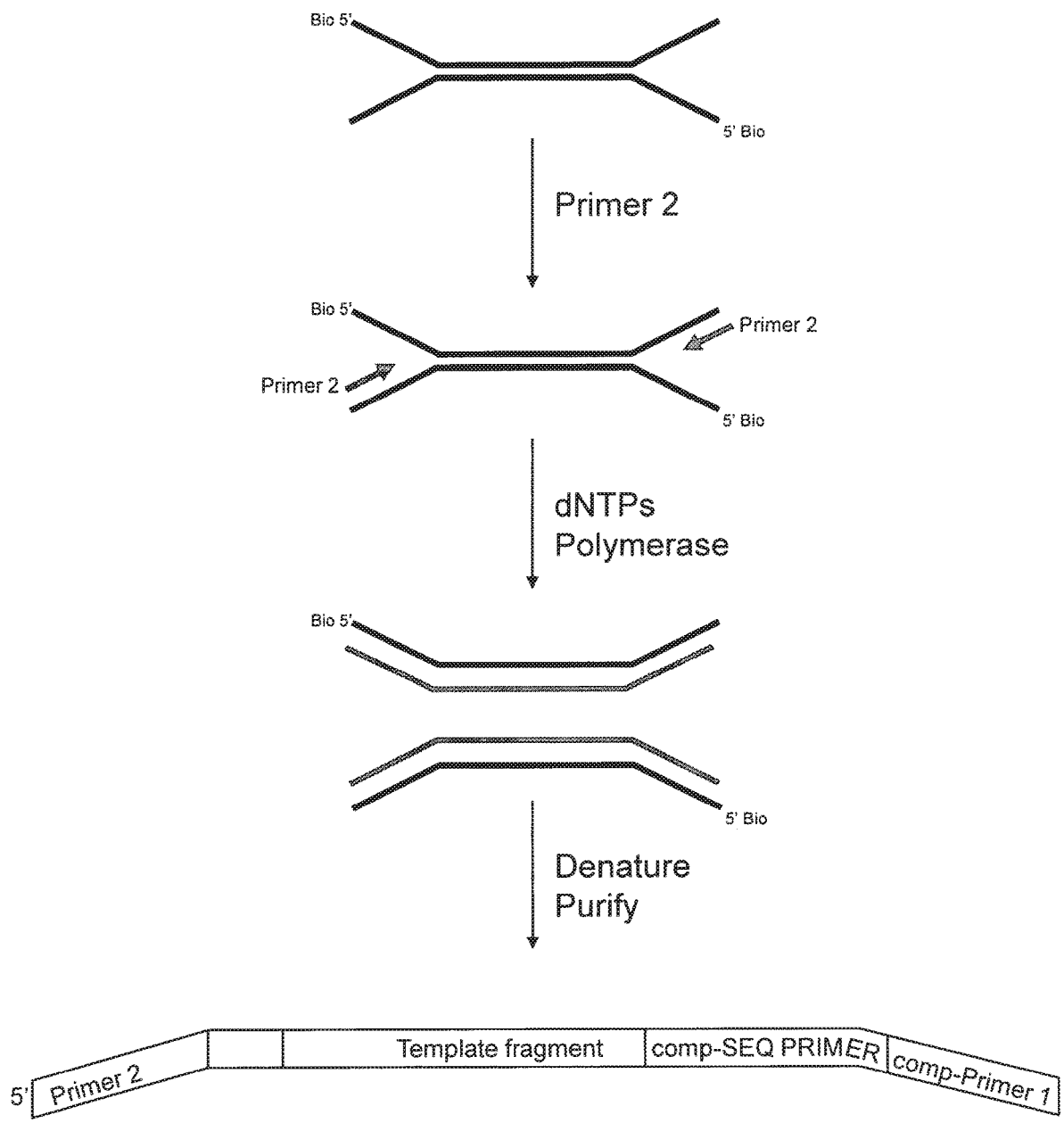

An oligonucleotide, herein referred to as PRIMER 2, which hybridises to the "comp-PRIMER 2" sequence on the oligo B strand of the adaptor-target constructs can be used in an initial primer extension reaction to generate a complementary copy of the adaptor-target strand attached to the bead. The resulting primer extension product forms a double-stranded duplex with its complementary adaptor-target strand attached to the bead and it can then be isolated and purified from its complementary adaptor-target strand on the bead by denaturation (FIG. 2C).

There are several standard methods for separating the strand of a DNA duplex by denaturation, including thermal denaturation, or preferably chemical denaturation in either 100 mM sodium hydroxide solution or formamide solution. The pH of a solution of single-stranded DNA in a sodium hydroxide solution collected from the supernatant of a suspension of magnetic beads can be neutralised by adjusting with an appropriate solution of acid, or preferably by buffer-exchange through a size-exclusion chromatography column pre-equilibrated in a buffered solution. The resulting solution contains a library of single-stranded DNA template molecules all of which comprise in order: 5' PRIMER 2 sequence, target DNA fragment, the complement of SEQ PRIMER sequence, then the complement of PRIMER 1 sequence. This template library can then be used on a solid-phase PCR platform that contains immobilised PRIMER 1 and PRIMER 2 oligonucleotides, or can be further amplified in solution using primer 1 and primer 2.

Figure 3:
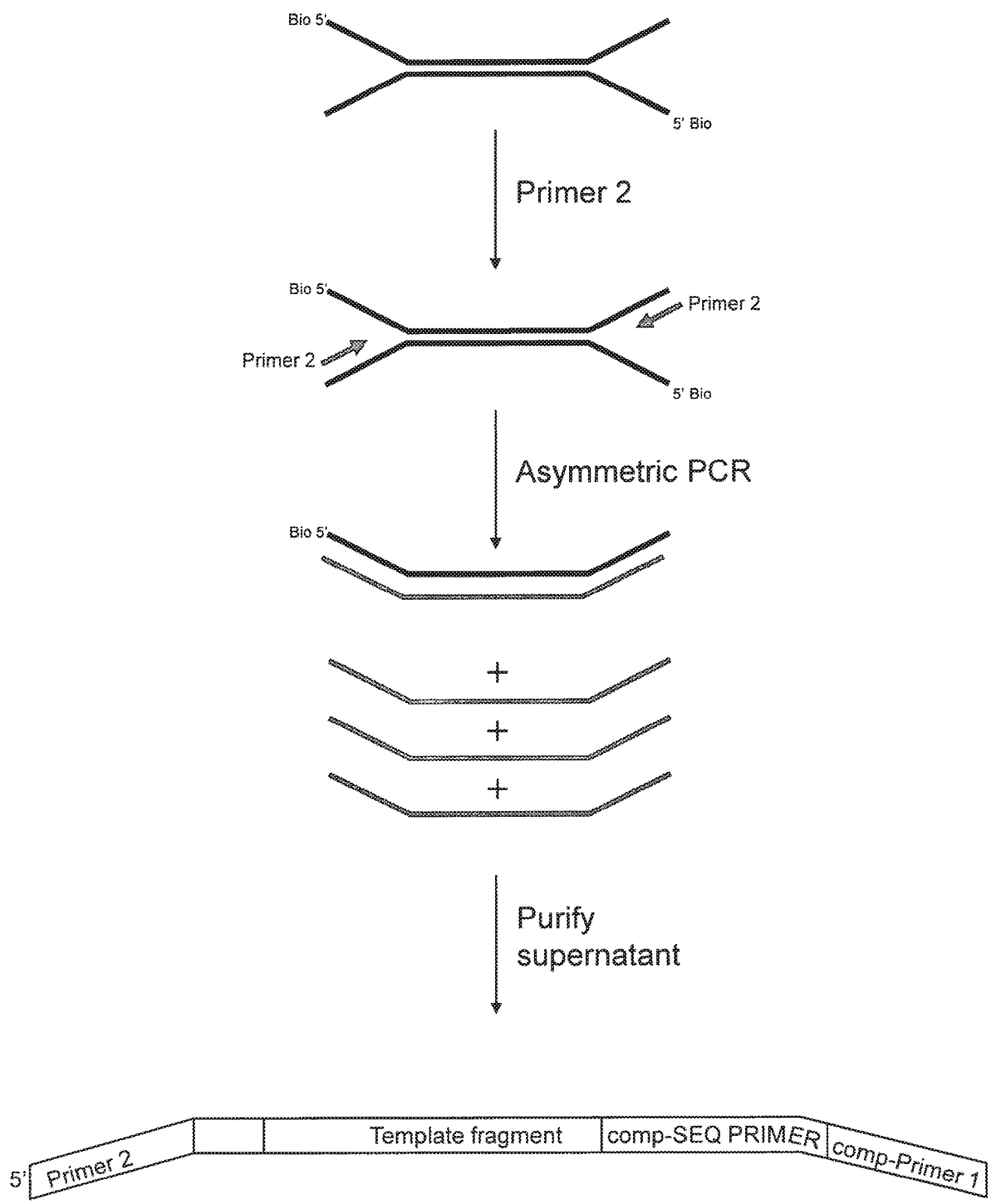
FIG. 3 illustrates an alternative embodiment of the invention in which adaptor-target constructs are subjected to multiple rounds of primer annealing and extension to generate multiple single-stranded copies of each adaptor-target construct. For simplicity, the primer extension steps are illustrated for a single adaptor-target construct.

FIG. 3 illustrates an alternative embodiment of the invention in which adaptor-target constructs prepared as described above with reference to FIG. 2C are subjected to multiple rounds of primer annealing and extension to generate multiple single-stranded copies of each adaptor-target construct. In this embodiment of the invention, the initial primer extension reaction on the bead immobilised adaptor-template molecules with PRIMER 2 is in effect replaced with an asymmetric PCR amplification with the PRIMER 2 oligonucleotide (FIG. 3), this being equivalent to multiple rounds of the same primer extension reaction. In this embodiment, multiple single-stranded copies of the bead-immobilised strands are generated in the supernatant of the bead suspension due to PCR thermocycling, hence a separate denaturation step is not necessary to recover the newly synthesised complementary copies of the bead-immobilised adaptor-target strands; the copies can be purified from the supernatant by standard methods, known to those skilled in the art.

Figure 4:
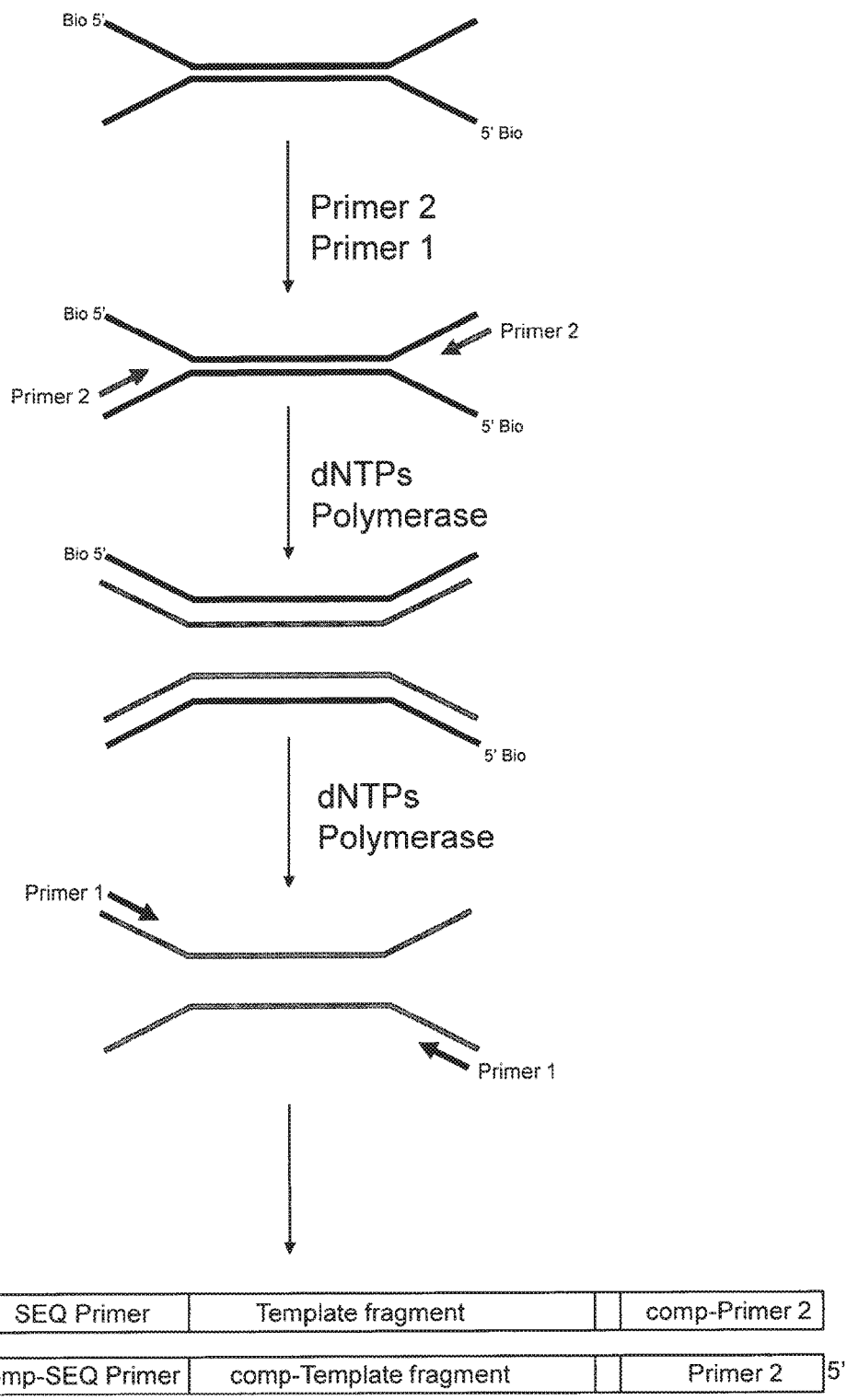
FIG. 4 illustrates a still further embodiment of the invention in which adaptor-target constructs are subjected to PCR amplification to generate multiple double-stranded copies of each adaptor-target construct. For simplicity, PCR amplification is illustrated for a single adaptor-target construct.

In another embodiment of the invention, illustrated in FIG. 4, the initial primer extension reaction on the bead-immobilised adaptor-target constructs with PRIMER 2 forms part of a standard (symmetric) PCR amplification with the PRIMER 2 and PRIMER 1 oligonucleotides. In this embodiment, multiple double-stranded copies of the bead-immobilised strands are generated in the supernatant of the bead suspension due to PCR thermocycling, hence a separate denaturation step is not necessary to recover the newly synthesised complementary copies of the bead-immobilised adaptor-target strands; the copies can be purified from the supernatant by standard methods, known to those skilled in the art.

In another embodiment of the invention, the adaptors are removed prior to amplification, as illustrated in FIG. 5. The forked adaptor does not contain a biotin group at the 5' end of the Oligo A strand. In this embodiment, fragmented DNA may be made blunt-ended by a number of methods known to those skilled in the art. In a particular method, the ends of the fragmented are polished with T4 DNA polymerase and Klenow polymerase, and then phosphorylated with polynucleotide kinase enzyme. A single 'A' deoxynucleotide is then added to both 3' ends of the DNA molecules with Taq polymerase or Klenow exo minus polymerase enzyme, producing a one-base 3' overhang that is complementary to the one-base 3' overhang on the double-stranded "ligatable" end of the forked adaptor. A ligation reaction between the forked adaptor and the DNA fragments is then performed, e.g. using T4 DNA ligase enzyme, which joins two copies of the adaptor to each DNA template molecule, one at either end.

The products of the ligation reaction can be purified from unligated adaptor by a number of means, including size-inclusion chromatography, preferably by electrophoresis through an agarose gel slab followed by excision of a portion of the agarose that contains DNA greater in size than the size of the adaptor. An aliquot of the purified template DNA is then bisulfite treated as in FIG. 2A, and used in a PCR amplification with the PRIMER 2 and PRIMER 1 oligonucleotides as described in FIG. 2A. The first PCR cycle will involve an initial primer extension reaction with primer 2 (not illustrated). The primers selectively amplify those template DNA molecules that have adaptors ligated on both ends. The product of the reaction is a library of double-stranded template molecules, each of which comprise in order on one of the duplex strands: 5' PRIMER 2 sequence, target DNA (template fragment), the complement of SEQ PRIMER sequence, then the complement of PRIMER 1 sequence. This library can then be amplified on a solid-phase PCR platform that contains immobilised PRIMER 1 and PRIMER 2 oligonucleotides, and compared with sequences derived from the portion of the sample that has not been bisulfate treated.

FIGS. 6A-6E illustrate further examples of forked mismatch adaptors for use in the method of the invention. In this embodiment the forked adaptor is formed by annealing two single-stranded oligonucleotides, herein referred to as "oligo C" and "oligo B". Both oligo B and oligo C need to have the cytosine bases methylated at the 5 position of the base. The oligonucleotides are partially complementary such that the 3' end of oligo C is complementary to the 5' end of oligo B. The 5' end of oligo C and the 3' end of oligo B are not complementary to each other. When the two oligos are annealed the resulting structure is double-stranded at one end (duplex region) and single-stranded at the other end (mismatch region) (FIG. 6A). The duplex region of the forked adaptor may be blunt-ended (FIG. 6D) or it may have an overhang. In the latter case, the overhang may be a 3' overhang (FIG. 6C) or a 5'overhang (FIG. 6B), and may comprise a single base or more than one base.

The 5' end of the duplex region of the forked adaptor is phosphorylated i.e. the 5' end of 'oligo B' (FIGS. 6A-6D) to provide a "ligatable" end. The 5' end of oligo C may be biotinylated or bear another functionality (X) that enables it to be captured on a surface, such as a bead. The 3' end of oligo B may also be biotinylated or bear another functionality (Y) that enables it to be captured on a surface (FIG. 6D).

The phosphodiester bonds that comprise the back-bone of the oligonucleotides may be replaced with non-enzymatically cleavable bonds such as phosphorothioate bonds. Preferably only the last, or last and penultimate, phosphodiester bonds at both the 3' and 5' ends of the oligonucleotides will be substituted with phosphorothioate bonds. Oligo C comprises the following: a sequence identical to that of a universal sequencing primer denoted "SEQ PRIMER" (or identical to part of the 3' end of the "SEQ PRIMER" sequence), plus an additional 'T' nucleotide on the 3' end. Oligo B comprises the following regions: a region at its 5' end that is complementary to a part of the 3' end of the SEQ PRIMER sequence in Oligo C, excluding the 'T' overhang of 'Oligo C', and a region at its 3' end which is complementary to that of a PCR amplification primer, herein referred to as the "comp-PRIMER 2" sequence, (FIG. 6E).

FIGS. 7A and 7B illustrate a further embodiment of the invention based on use of the forked adaptors illustrated in FIGS. 6A-6E. In this embodiment, adaptor-target constructs are prepared substantially as described above with reference to FIG. 2A (FIG. 5 without the adaptor removal), except that the adaptors illustrated in FIGS. 6A-6E are used (FIG. 7A). Again, a portion of the sample (i.e., a subportion or part of the sample) is treated with bisulfite, and the resultant bisulfite treated and bisulfite untreated (control) portions are processed for sequencing.

As used herein, the term "untreated" or "control" portion of a sample refers to a portion of the sample not exposed to the indicated treatment. The term may, therefore, be used to refer to a portion of a sample that has not been treated with, for example, bisulfite, but rather has been exposed to or incubated in an appropriate control buffer that is essentially inert with respect to bisulfite induced activity.

Each portion of the sample is used in a standard solution-phase PCR amplification with "tailed" primer oligonucleotides. Tailed primers are primers that only hybridize via their 3' end to a target sequence, leaving a 5' non-hybridised tail. When used in amplifications by PCR, the initial round of PCR amplification (i.e. the first and second primer extension reactions) rely on binding of the 3' ends of the tailed primers to cognate primer-binding sequences in the adaptor regions of the adaptor-target constructs. The 5' non-hybridising tails derived from the tailed primers act as templates in subsequent PCR cycles and are therefore copied into the resultant double-stranded PCR products.

In the present embodiment, either one or both of the primers used in the amplification reaction can be "tailed" primers. In one embodiment, the primers used are denoted PRIMER 3 and PRIMER 4, where PRIMER 3 consists of a 5' tail sequence, and a 3' sequence that is complementary to the "comp PRIMER 2" sequence in the forked adaptor; and PRIMER 4 consists of a 5' tail sequence, and a 3' sequence that is identical to the 5' end of the SEQ PRIMER sequence present in the mismatch region of the forked adaptor. Following amplification by PCR, the tail sequences are incorporated into the copies of the adaptor-target DNA construct.

In one embodiment of the invention, the tail sequences on PRIMER 3 and PRIMER 4 are non-identical sequences. The sequence of surface-immobilised primers to be used on a subsequent solid-phase DNA amplification platform can then be designed based on the tail sequence of PRIMER 3 and the tail sequence of PRIMER 4 (FIG. 7B).

In another embodiment of the invention, the tail sequences on PRIMER 3 and PRIMER 4 are identical sequences. The products of the solution-phase PCR will thus have the same sequence at their ends, namely the common tail sequence of PRIMER 3 and PRIMER 4. This common tail sequence can then be used as the basis on which to design the sequence of a single surface-immobilised primer on a solid-phase DNA amplification platform. Subsequent surface amplification of the library of templates may thus be performed using a single PCR primer immobilised on the surface.

FIGS. 8A-8E illustrate alternative embodiments of mismatch adaptors for use in the method of the invention, wherein the mismatch region takes the form of a bubble. These "modified" forked adaptors may be designed to enable solid-phase amplification of templates using a single surface bound primer. The adaptor is formed by annealing two single-stranded oligonucleotides, herein referred to as "oligo D" and "oligo E". Both oligonucleotides D and E are modified such that all the cytosine bases are methylated at the 5 position. The oligonucleotides are partially complementary such that the 3' end of oligo D is complementary to the 5' end of oligo E, and the 5' end of oligo D is complementary to the 3' end of oligo E, however, the central portions of oligo D and oligo E are non-complementary. When oligo D and oligo E are annealed, the resulting structure is double stranded at both ends (duplex regions) and single stranded in the middle (mismatch bubble region) and is referred to herein as the "modified Forked adaptor" (FIG. 8A).

One end of the modified forked adaptor is modified to prevent ligation of a DNA molecule to this end. Such modifications are known to those skilled in the art. The other "ligatable" end may be blunt-ended (FIG. 8D) or may have an overhang. In the latter case, the overhang may be a 3' overhang (FIG. 8C) or a 5 'overhang (FIG. 8B), and may comprise a single base or more than one base. The 5' strand of the ligatable end is phosphorylated i.e. the 5' end of oligo E (FIGS. 8A-8D). The 5' end of oligo D may be biotinylated or bear another functionality that enables it to be captured on a surface, such as a bead. The 3' end of oligo E may be biotinylated or bear another functionality that enables it to be captured on a surface (FIG. 8D). The modifications to prevent ligation (Z,W) may be the same as or different to the surface capture functionalities (X,Y).

The phosphodiester bonds that comprise the backbone of the oligonucleotides may be replaced with non-enzymatically cleavable bonds such as phosphorothioate bonds. In a particular embodiment, only the last, or last and penultimate, phosphodiester bonds at both the 3' and 5' ends of the oligonucleotides are substituted with phosphorothioate bonds.

In a particular embodiment of the invention, oligo E is phosphorylated at its 5' end and the 3' end of oligo D contains a single base 3' overhang comprising a "T" nucleotide. Oligo D comprises two sequences: a sequence at its 5' end which is identical to that of a universal amplification primer, referred to herein as "PRIMER 5" sequence, next to a sequence identical to that of a universal sequencing primer denoted "SEQ PRIMER" sequence plus the additional "T" nucleotide on the 3' end. Oligo E comprises three sequences: a sequence at its 5' end that is complementary to only part of the 3' end of the SEQ PRIMER sequence in Oligo D, excluding the 'T' overhang of Oligo D, a central sequence non-complementary to any part of Oligo D, and a 3' end that is complementary to the "PRIMER 5" sequence of Oligo D (FIG. 8E).

FIGS. 9A and 9B illustrate a still further embodiment of the invention based on use of the alternative adaptors illustrated in FIGS. 8A-8E. In this embodiment adaptor-target constructs may be prepared substantially as described above in relation to FIG. 5, except that the modified forked adaptors illustrated in FIGS. 8A-8E are used. The adapters can be removed and a portion of the sample treated with bisulfite. Both the bisulfite treated and untreated aliquots of the adaptor-target constructs are used in a solution-phase PCR amplification using PRIMER 5 oligonucleotide to selectively amplify those ligation products that have the modified adaptor on both ends (FIG. 9B). The product of the solution-phase PCR can then be purified and amplified on a solid-phase platform with a single immobilised primer, e.g. PRIMER 5. Inclusion of the mismatch bubble sequence in oligo E ensures that all products of this solid-phase amplification will contain common sequencing primer binding sequences on one strand only, enabling sequencing using a universal sequencing primer which anneals to this common sequence.

Solid-Phase Amplification

Once formed, the library of templates prepared according to the methods described above can be used for solid-phase nucleic acid amplification.

Thus, in further aspects the invention provides a method of solid-phase nucleic acid amplification of template polynucleotide molecules which comprises preparing a library of template polynucleotide molecules which have known sequences at their 5' and 3' ends using a method according to the first aspect of the invention described herein and carrying out a solid-phase nucleic acid amplification reaction wherein said template polynucleotide molecules are amplified.

The term 'solid-phase amplification' as used herein refers to any nucleic acid amplification reaction carried out on or in association with a solid support such that all or a portion of the amplified products are immobilised on the solid support as they are formed. In particular, the term encompasses solid-phase polymerase chain reaction (solid-phase PCR) and solid phase isothermal amplification which are reactions analogous to standard solution phase amplification, except that one or both of the forward and reverse amplification primers is/are immobilised on the solid support. Solid phase PCR covers systems such as emulsions, wherein one primer is anchored to a bead and the other is in free solution, and colony formation in solid phase gel matrices wherein one primer is anchored to the surface, and one is in free solution.

The invention encompasses "solid-phase" amplification methods in which only one amplification primer is immobilised (the other primer usually being present in free solution), as well as the solid support to be provided with both the forward and the reverse primers immobilised. In practice, there will be a "plurality" of identical forward primers and/or a "plurality" of identical reverse primers immobilised on the solid support, since the amplification process requires an excess of primers to sustain amplification. References herein to forward and reverse primers are to be interpreted accordingly as encompassing a "plurality" of such primers unless the context indicates otherwise.

As will be appreciated by the skilled reader, any given amplification reaction requires at least one type of forward primer and at least one type of reverse primer specific for the template to be amplified. In certain embodiments, however, the forward and reverse primers may comprise template-specific portions of identical sequence, and may have entirely identical nucleotide sequence and structure (including any non-nucleotide modifications). In other words, it is possible to carry out solid-phase amplification using only one type of primer, and such single-primer methods are encompassed within the scope of the invention. Other embodiments may use forward and reverse primers which contain identical template-specific sequences but which differ in some other structural features. For example one type of primer may contain a non-nucleotide modification which is not present in the other.

In other embodiments of the invention the forward and reverse primers may contain template-specific portions of different sequence.

In all embodiments of the invention, amplification primers for solid-phase amplification are preferably immobilised by covalent single point attachment to the solid support at or near the 5' end of the primer, leaving the template-specific portion of the primer free for annealing to its cognate template and the 3' hydroxyl group free for primer extension. Any suitable covalent attachment means known in the art may be used for this purpose. The chosen attachment chemistry will depend on the nature of the solid support, and any derivatisation or functionalisation applied thereto. The primer itself may include a moiety, which may be a non-nucleotide chemical modification, to facilitate attachment. In a particular embodiment, the primer may include a sulphur-containing nucleophile, such as phosphorothioate or thiophosphate, at the 5' end. In the case of solid-supported polyacrylamide hydrogels (as described below), this nucleophile will bind to a bromoacetamide group present in the hydrogel. A particular means of attaching primers and templates to a solid support is via 5' phosphorothioate attachment to a hydrogel comprised of polymerised acrylamide and N-(5-bromoacetamidylpentyl) acrylamide (BRAPA), as described in WO05065814, the contents of which are included herein by reference in their entirety.

Certain embodiments of the invention may make use of solid supports comprised of an inert substrate or matrix (e.g. glass slides, polymer beads, etc) which has been "functionalised", for example by application of a layer or coating of an intermediate material comprising reactive groups which permit covalent attachment to biomolecules, such as polynucleotides. Examples of such supports include, but are not limited to, polyacrylamide hydrogels supported on an inert substrate such as glass. In such embodiments, the biomolecules (e.g. polynucleotides) may be directly covalently attached to the intermediate material (e.g. the hydrogel), but the intermediate material may itself be non-covalently attached to the substrate or matrix (e.g. the glass substrate). The term "covalent attachment to a solid support" is to be interpreted accordingly as encompassing this type of arrangement.

The library of templates prepared according to the first aspect of the invention can be used to prepare clustered arrays of nucleic acid colonies, analogous to those described in WO 00/18957 and WO 98/44151, by solid-phase amplification. The terms "cluster" and "colony" are used interchangeably herein to refer to a discrete site on a solid support comprised of a plurality of identical immobilised nucleic acid strands and a plurality of identical immobilised complementary nucleic acid strands. The term "clustered array" refers to an array formed from such clusters or colonies. In this context the term "array" is not to be understood as requiring an ordered arrangement of clusters.

The term solid phase, or surface, is used to mean either a planar array wherein primers are attached to a flat surface, for example, glass, silica or plastic microscope slides or similar flow cell devices; beads, wherein either one or two primers are attached to the beads and the beads are amplified; or an array of beads on a surface after the beads have been amplified.

Clustered arrays can be prepared using either a process of thermocycling, as described in patent WO9844151, or a process whereby the temperature is maintained as a constant, and the cycles of extension and denaturing are performed using changes of reagents. Such isothermal amplification methods are described in patent application numbers WO0246456 and US20080009420 (WO07107710) (Isothermal methods for creating clonal single molecule arrays) and the contents of these documents is included herein by reference. The lower temperatures required in the isothermal process render this approach particularly advantageous.

Use in Sequencing/Methods of Sequencing

The invention also encompasses methods of sequencing amplified nucleic acids generated by solid-phase amplification. Thus, the invention provides a method of nucleic acid sequencing comprising amplifying a library of nucleic acid templates using solid-phase amplification as described above and carrying out a nucleic acid sequencing reaction to determine the sequence of the whole or a part of at least one amplified nucleic acid strand produced in the solid-phase amplification reaction. As will be apparent to the skilled reader, references herein to a particular nucleic acid sequence may, depending on the context, also refer to nucleic acid molecules which comprise the nucleic acid sequence. Sequencing of a target fragment means that a read of the chronological order of bases is established. The bases do not need to be contiguous, nor does every base on the entire fragment have to be sequenced.

Sequencing can be carried out using any suitable sequencing technique, wherein nucleotides are added successively to a free 3' hydroxyl group, resulting in synthesis of a polynucleotide chain in the 5' to 3' direction. The nature of the nucleotide added is preferably determined after each nucleotide addition. Sequencing techniques using sequencing by ligation, wherein not every contiguous base is sequenced, and techniques such as massively parallel signature sequencing (MPSS) where bases are removed from, rather than added to the strands on the surface are also within the scope of the invention, as are techniques using detection of pyrophosphate release (pyrosequencing). Such pyrosequencing based techniques are particularly applicable to sequencing arrays of beads wherein the beads have been amplified in an emulsion such that a single template from the library molecule is amplified on each bead.

The initiation point for the sequencing reaction may be provided by annealing of a sequencing primer to a product of the solid-phase amplification reaction. In this connection, one or both of the adaptors added during formation of the template library may include a nucleotide sequence which permits annealing of a sequencing primer to amplified products derived by whole genome or solid-phase amplification of the template library.

The products of solid-phase amplification reactions wherein both forward and reverse amplification primers are covalently immobilised on the solid surface are so-called 'bridged' structures formed by annealing of pairs of immobilised polynucleotide strands and immobilised complementary strands, both strands being attached to the solid support at the 5' end. Arrays comprised of such bridged structures provide inefficient templates for nucleic acid sequencing, since hybridisation of a conventional sequencing primer to one of the immobilised strands is not favoured relative to annealing of this strand to its immobilised complementary strand under standard conditions for hybridisation.

In order to provide more suitable templates for nucleic acid sequencing it is preferred to remove or displace substantially all or at least a portion of one of the immobilised strands in the 'bridged' structure in order to generate a template which is at least partially single-stranded. The portion of the template which is single-stranded will thus be available for hybridisation to a sequencing primer. The process of removing all or a portion of one immobilised strand in a 'bridged' double-stranded nucleic acid structure may be referred to herein as 'linearisation'.

Bridged template structures may be linearised by cleavage of one or both strands with a restriction endonuclease or by cleavage of one strand with a nicking endonuclease. Other methods of cleavage can be used as an alternative to restriction enzymes or nicking enzymes, including inter alia chemical cleavage (e.g. cleavage of a diol linkage with periodate), cleavage of abasic sites by cleavage with endonuclease (for example 'USER', as supplied by NEB, part number M5505S), or by exposure to heat or alkali, cleavage of ribonucleotides incorporated into amplification products otherwise comprised of deoxyribonucleotides, photochemical cleavage or cleavage of a peptide linker.

It will be appreciated that a linearization step may not be essential if the solid-phase amplification reaction is performed with only one primer covalently immobilised and the other in free solution.

Following the cleavage step, regardless of the method used for cleavage, the product of the cleavage reaction may be subjected to denaturing conditions in order to remove or displace the portion(s) of the cleaved strand(s) that are not attached to the solid support. Suitable denaturing conditions, for example sodium hydroxide solution, formamide solution or heat, will be apparent to the skilled reader with reference to standard molecular biology protocols (Sambrook et al., 2001, *Molecular Cloning, A Laboratory Manual*, 3rd Ed, Cold Spring Harbor Laboratory Press, Cold Spring Harbor Laboratory Press, NY; Current Protocols, eds Ausubel et al.). Denaturation results in the production of a sequencing template which is partially or substantially single-stranded. A sequencing reaction may then be initiated by hybridisation of a sequencing primer to the single-stranded portion of the template.

Thus, the invention encompasses methods wherein the nucleic acid sequencing reaction comprises hybridising a sequencing primer to a single-stranded region of a linearised amplification product, sequentially incorporating one or more nucleotides into a polynucleotide strand complementary to the region of amplified template strand to be sequenced, identifying the base present in one or more of the incorporated nucleotide(s) and thereby determining the sequence of a region of the template strand.

One preferred sequencing method which can be used in accordance with the invention relies on the use of modified nucleotides having removable 3' blocks, for example as described in WO04018497 and U.S. Pat. No. 7,057,026, the contents of which are incorporated herein by reference in their entirety. Once the modified nucleotide has been incorporated into the growing polynucleotide chain complementary to the region of the template being sequenced there is no free 3'-OH group available to direct further sequence extension and therefore the polymerase can not add further nucleotides. Once the nature of the base incorporated into the growing chain has been determined, the 3' block may be removed to allow addition of the next successive nucleotide. By ordering the products derived using these modified nucleotides it is possible to deduce the DNA sequence of the DNA template. Such reactions can be done in a single experiment if each of the modified nucleotides has a different label attached thereto, known to correspond to the particular base, to facilitate discrimination between the bases added during each incorporation step. Alternatively, a separate reaction may be carried out containing each of the modified nucleotides separately.

The modified nucleotides may comprise a label to facilitate their detection. In a particular embodiment, this is a fluorescent label. Each nucleotide type may comprise a different fluorescent label, for example as described in U.S. Provisional Application No. 60/801,270 (WO07135368) (Novel dyes and the use of their labelled conjugates). The detectable label need not, however, be a fluorescent label. Any label can be used which allows the detection of an incorporated nucleotide.

One method for detecting fluorescently labelled nucleotides comprises using laser light of a wavelength specific for the labelled nucleotides, or the use of other suitable sources of illumination. The fluorescence from the label on the nucleotide may be detected by a CCD camera or other suitable detection means. Suitable instrumentation for recording images of clustered arrays is described in U.S. Provisional Application No. 60/788,248 (WO07123744) (Systems and Devices for Sequence by Synthesis Analysis).

The invention is not intended to be limited to use of the sequencing method outlined above, as essentially any sequencing methodology which relies on successive incorporation of nucleotides into a polynucleotide chain can be used. Suitable alternative techniques include, for example, Pyrosequencing™, FISSEQ (fluorescent in situ sequencing), MPSS and sequencing by ligation-based methods, for example as described is U.S. Pat. No. 6,306,597.

Sequencing data obtained from each array, whether on a sample pooled after the amplification reaction such that the treated and untreated portions are sequenced on the same array, or on separate arrays for each portion, will reveal which cytosine bases have been converted to uracil bases, and therefore which bases in the sample contained a methylated cytosine that is resistant to conversion. Analysis of the sequence reads across the whole nucleic acid sample will, therefore, provide a picture of the global methylation status of essentially every cytosine base in the sample.

Kits

The invention also relates to kits for use in methylation analysis using the method of the first aspect of the invention.

Preferred embodiments of the kit comprise at least a supply of a universal methylated mismatch adaptor as defined herein, plus a supply of at least one amplification primer which is capable of annealing to the adaptor and priming synthesis of an extension product, which extension product would include any target sequence ligated to the adaptor when the adaptor is in use.

The particular features of the "mismatch" adaptors for inclusion in the kit are as described elsewhere herein in relation to other aspects of the invention, including structures of the forked adaptors. The structure and properties of appropriate amplification primers are well known to those skilled in the art. Suitable primers of appropriate nucleotide sequence for use with the adaptors included in the kit can be readily prepared using standard automated nucleic acid synthesis equipment and reagents in routine use in the art. The kit may include a supply of one single type of primer or separate supplies (or even a mixture) of two different primers, for example, a pair of PCR primers suitable for PCR amplification of templates modified with the universal adaptor in solution phase and/or on a suitable solid support.

In one embodiment, the kit may include supplies of different primer-pairs for use in solution phase and solid phase PCR. In this context the "different" primer-pairs may be of substantially identical nucleotide sequence but differ with respect to some other feature or modification, such as for example surface-capture moieties, etc. In other embodiments, the kit may include a supply of primers for use in an initial primer extension reaction and a different primer-pair (or pairs) for solution and/or solid phase PCR amplification.

Adaptors and/or primers may be supplied in the kits ready for use, or as concentrates requiring dilution before use, or even in a lyophilised or dried form requiring reconstitution prior to use. If required, the kits may further include a supply of a suitable diluent for dilution or reconstitution of the primers. Optionally, the kits may further comprise supplies of reagents, buffers, enzymes, dNTPs, etc. for use in carrying out PCR amplification. Suitable (but non-limiting) examples of such reagents are as described in the Materials and Methods sections of the accompanying Examples. Further components which may optionally be supplied in the kit include flow cells for cluster preparation and "universal" sequencing primers suitable for sequencing templates prepared using the universal adaptors and primers.

While the foregoing invention has been described in some detail for purposes of clarity and understanding, it will be clear to one skilled in the art from a reading of this disclosure that various changes in form and detail can be made without departing from the true scope of the invention. All publications, patents, patent applications, or other documents cited in this application are incorporated by reference in their entirety for all purposes to the same extent as if each individual publication, patent, patent application, or other document were individually indicated to be incorporated by reference for all purposes.

EXAMPLES

In one embodiment of the invention, the genomic DNA is fragmented by limit digestion with a methylation-insensitive restriction enzyme rather than by random hydrodynamic shearing. After size fractionation on an agarose gel, a narrow size window is isolated which constitutes only a small portion of the genome. By careful size-selection, essentially the same genomic subfraction can be isolated from different input samples and compared by sequencing. This reduced representation approach has been used for comparative sequencing (SNP detection; Altshuler et al., Nature 407:513-516 (2000) and has been proposed as a high-throughput method for comparative DNA methylation analysis (Meissner et al., Nucleic Acids Res. 33:5868-5877, 2005). In the exemplary embodiment illustrated in FIG. 10A, genomic DNA from 4 different mouse cell types is digested with the restriction enzyme MspI and size selected to 40-220 bp resulting in a reduced representation of the mouse genome that is enriched for CpG dinucleotides and CpG islands. As shown in FIG. 10B, the size selected fragments are equipped with the aforementioned methylated forked adapters, bisulfite converted and sequenced as described elsewhere in this document. After mapping the bisulfite sequencing reads by aligning them to the mouse reference genome, methylated cytosines are displayed as bisulfite-resistant Cs. The MspI Reduced Representation Bisulfite Sequencing approach has been used for comparative methylation profiling of four different mouse cell types resulting in redundant coverage of almost one million distinct CpG dinucleotides in each cell type with more than 800,000 CpGs covered in all four cell types (FIG. 10C).

MspI RRBS library construction. Ten µg mouse genomic DNA was digested with 100 U of MspI (NEB) in a 500 µl reaction overnight at 37° C. Digested DNA was phenol extracted, ethanol precipitated and size selected on a 4% NuSieve 3:1 Agarose gel (Lonza). DNA marker lanes were excised from the gel and stained with SYBR Green (Invitrogen). For each sample, two slices containing DNA fragments of 40-120 bp and 120-220 bp, respectively, were excised from the unstained preparative portion of the gel. DNA was recovered using Easy Clean DNA spin filters (Primm labs, Boston, Mass., USA), phenol extracted and ethanol precipitated. The two size fractions were kept apart throughout the procedure including the final sequencing. Size-selected MspI fragments were filled in and 3'-terminal A extended in a 50 µl reaction containing 20 U Klenow exo⁻ (NEB), 0.4 mM dATP, 0.04 mM dGTP, and 0.04 mM 5-methyl-dCTP (Roche) in 1×NEB buffer 2 (15 min at room temperature followed by 15 min at 37° C.), phenol extracted and ethanol precipitated with 10 µg glycogen (Roche) as a carrier. Ligation to pre-annealed Illumina adapters containing 5'-methyl-cytosine instead of cytosine (Illumina) was performed using the Illumina DNA preparation kit and protocol. QIAquick (QIAGEN) cleaned-up, adapter-ligated fragments were bisulfite-treated using the EpiTect Bisulfite Kit (QIAGEN) with minor modifications: The bisulfite conversion time was increased to approximately 14 hours by adding 3 cycles (5 min of denaturation at 95° C. followed by 3 hours at 60° C.). After bisulfite conversion, the single-stranded uracil-containing DNA was eluted in 20 µl of EB buffer. Analytical (25 µl) PCR reactions containing 0.5 µl of bisulfite-treated DNA, 5 pmol each of genomic PCR primers 1.1 and 2.1 (Illumina) and 2.5 U PfuTurboCx Hotstart DNA polymerase (Stratagene) were set up to determine the minimum number of PCR cycles required to recover enough material for sequencing. Preparative scale (8×25 µl) PCR was performed using the same PCR profile: 5 min at 95° C., n×(30 s at 95° C., 20 s at 65° C., 30 s at 72° C.) followed by 7 min at 72° C., with n ranging from 18 to 24 cycles. QIAquick purified PCR products were subjected to a final size selection on a 4% NuSieve 3:1 Agarose gel. SYBR Green-stained gel slices containing adapter-ligated fragments of 130-210 bp or 210-310 bp in size were excised. RRBS library material was recovered from the gel (QIAquick) and sequenced on an Illumina 1G Genome Analyzer.

The sequences of the relevant adapters are as follows, where every cytosine base contains the 5-methyl group

```
                                             (SEQ ID No. 1)
    5' P-GATCGGAAGAGCTCGTATGCCGTCTTCTGCTTG (SEQ ID NO. 2)
    5' ACACTCTTTCCCTACACGACGCTCTTCCGATCT
```

The sequences of the two PCR primers are as follows

```
                                             (SEQ ID No. 3)
5' AATGATACGGCGACCACCGAGATCTACACTCTTTCCCTACACGACGC
TCTTCCGATCT (SEQ ID NO. 4)
    5' CAAGCAGAAGACGGCATACGAGCTCTTCCGATCT
```

The 3' terminal residues of these sequences comprise a phosphorothioate linkage. The oligonucleotides are exonucleases treated with Exonuclease I and HPLC purified as described below:

Exonuclease I (E. coli) NEB M0293S 20,000 Units/ml
Exonuclease I Storage Conditions:
  100 mM NaCl, 10 mM Tris-HCl (pH 7.5), 0.5 mM EDTA, 5 mM 2-mercaptoethanol, 100 µg/ml BSA and 50% glycerol
1× Exonculease Reaction Buffer
  67 mM Glycine-KOH
  6.7 mM MgCl₂
  10 mM 2-mercaptoethanol
  (pH 9.5 @ 25° C.)
Protocol:
  DNA Primers with a phosphorothioate at the n−1 position (5×85 ul of each Primer (approx 25 µM) were aliquoted into eppendorf tubes. 10 µl of 10× Exonuclease I Reaction Buffer and 5 µl of Exonuclease I was added to each tube. Each Eppendorf tube was placed in a rack and stored in an oven set at 37° C. for 16 hours. After 16 hr, the tubes were placed on a hotblock set at 80° C. for 2 minutes. Then the solutions from the eppendorfs were passed through P6 Bio Rad columns and spun in a centrifuge at 2000 rpm for 2 minutes. An extra 20 µl of H₂O was added and the columns respun. The filtered solutions were placed into a speedvac and evaporated until each was at 20 µl, and the fractions combined. The pooled fractions were injected into a reverse phase HPLC system, and the main peak was collected. The collected fractions were evaporated to dryness in a speedvac, 50 µl of water was added and the fraction was subjected again to evaporation to dryness. The resulting pellets were dissolved in 50 µl of water, pooled and the UV measurement taken to determine the concentration of the oligonucleotide.

The samples were used to isothermally amplify clusters according to the methods below:

Cluster creation was carried out using an Illumina Cluster Station. To obtain single stranded templates, adapted DNA was first denatured in NaOH (to a final concentration of 0.1N) and subsequently diluted in cold (4° C.) hybridisation buffer (5×SSC+0.05% Tween 20) to working concentrations of 2-4 pM, depending on the desired cluster density/tile. 120 µl of each sample were primed through each lane of a Solexa flowcell (60 µl/min) mounted on a Solexa Cluster Station, upon which all subsequent steps are performed. The temperature was ramped to 95° C. for 60 s and slowly decreased to 40° C. at a rate of 0.05° C./sec to enable annealing to complementary adapter oligonucleotides immobilised on the flowcell surface (oligo A: 5'-PS-TTTTTTTTTT-(diol)3-AATGATACGGCGAC-CACCGA-3' (SEQ ID No. 5); oligo B: 5'-PS-TTTTTTTTTTCAAGCAGAAGACGGCATACGA-3' (SEQ ID No. 6)). Hybridised template strands were extended using Taq polymerase (0.25 U/µl, 200 uM dNTP) in 1× amplification premix (20 mM Tris pH 8.8, 10 mM (NH4)2SO4, 2 mM MgSO4, 0.1% Triton X-100, 2 M betaine) to generate their surface-bound complement. The samples were then denatured using formamide and washed with wash buffer (0.3×SSC) to remove the initial seeded template. The remaining single stranded copy was the starting point for cluster creation. Clusters were amplified under isothermal conditions at 60° C. for 30 cycles using successive rounds of amplification premix mix (28 µl, 15 µl/min), amplification mix (28 µl at 15 µl/min 0.08 U/µl Bst polymerase+200 uM dNTPs in 1× amplification premix) and formamide (36 µl at 15 µl/min) Following amplification, clusters were washed with storage buffer (5×SSC). At this stage, clusters were either stored at 4° C. until required for sequencing or immediately prepared for sequencing.

Linearisation of surface-immobilised complementary oligo-A was achieved by incubation with linearization mix (100 mM sodium periodate, 10 mM 3-aminopropan-1-ol, 20 mM Tris pH 8.0, 50% v/v formamide) for 20 minutes at 20° C. followed by a water wash. All exposed 3'-OH termini of DNA, either from the extended template or unextended surface oligonucleotides were blocked by dideoxy chain termination using a terminal transferase (0.25 U/µl, 2.4 uM ddNTP, 50 mM potassium acetate, 20 mM Tris acetate, 10 mM magnesium acetate, 1 mM dithiothreitol pH 7.9, 37° C., 30 minute incubation). Linearised and blocked clusters were denatured with 0.1N NaOH prior to hybridisation of the sequencing primer (0.5 uM in hybridisation buffer, sequence=5' ACACTCTTTCCCTACACGACGCTCTTCC-GATCT (SEQ ID No. 7)). Processed flowcells were transferred to the Illumina Genome Analyser for sequencing.

All processes were conducted as described in the Illumina Genome Analyser operating manual. The flowcell was mounted to the analyser, primed with sequencing reagents: position #1=incorporation mix (1 uM NTP mix, 0.015 µg/ml SBS polymerase, 50 mM Tris pH 9.0, 50 mM NaCl, 6 mM MgSO4, 1 mM EDTA, 0.05% Tween 20); position #2=spare (MilliQ water only); position #3=scan mix (100 mM Tris pH 7.0, 50 mM sodium acsorbate); position #4=High salt wash (5×SSC, 0.05% Tween 20); position #5=incorporation buffer (50 mM Tris pH 9.0, 50 mM NaCl, 1 mM EDTA, 0.05% Tween 20); position #6=cleavage mix (100 mM TCEP, 100 mM Tris pH 9.0, 100 mM NaCl, 50 mM sodium ascorbate, 0.05% Tween 20); position #7=cleavage buffer (100 mM Tris pH 9.0, 100 mM NaCl, 0.05% Tween 20); position #8=spare. Flowcells were sequenced using standard sequencing recipes for 37-cycle experiments. Data was analysed using the standard analysis pipeline.

Each cycle of the sequencing recipe is as follows:

Sequencing of the clusters from the above illustrative protocol was carried out using modified nucleotides prepared as described in International patent application WO 2004/018493, and labeled with four spectrally distinct fluorophores, as described in PCT application number PCT/GB2007/001770, published as WO07135368. Sequencing of clusters is described in more detail in patent WO06064199. The contents of the above-listed documents are incorporated herein by reference in their entireties.

A mutant 9° N polymerase enzyme (an exo− variant including the triple mutation L408Y/Y409A/P410V and C223S) (SBS polymerase) was used for the nucleotide incorporation steps.

Incorporation: Prime with Incorporation buffer, 125 µL/channel; 60 µL/minutes, Heat to 60° C.

Treat with Incorporation mix, 75 µL/channel; 60 µL/minutes.

Wait for a total of 15 minutes in addition to pumping fresh Incorporation mix, 25 µL/channel; 60 µL/minutes, every 4 minutes.

Cool to 20° C.

Wash with Incorporation buffer, 75 µL/channel; 60 µL/minutes.

Wash with 5×SSC/0.05% Tween 20, 75 µL/channel; 60 µL/minutes

Prime with imaging buffer, 100 µL/channel; 60 µL/minutes

Scan in 4 colors at RT.

Cleavage: Prime with Cleavage buffer (0.1M Tris pH 7.4, 0.1M NaCl and 0.05% Tween 20), 125 µL/channel; 60 µL/minutes.

Heat to 60° C.

Treat the clusters with Cleavage mix (100 mM TCEP in Cleavage buffer), 75 µL/channel; 60 µL/minutes.

Wait for a total of 15 minutes in addition to pumping fresh cleavage mix, 25 µL/channel; 60 µL/minutes, every 4 minutes.

Cool to 20° C.

Wash with Enzymology buffer.

Wash with 5×SSC/0.05% Tween 20.

Repeat the process of Incorporation and Cleavage for as many cycles as required.

Incorporated nucleotides were detected using the Illumina genome analyzer, a Total Internal Reflection based fluorescent CCD imaging apparatus described in "Systems and Devices for Sequence by Synthesis Analysis," U.S. Ser. No. 60/788,248, filed Mar. 31, 2006 and corresponding PCT application PCT/US07/07991, published as WO07123744, the contents of which are incorporated herein by reference in their entirety.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

The invention claimed is:

1. A kit for use in preparing a sequencing library, the kit comprising adaptor polynucleotides, wherein:
   each of the adaptor polynucleotides comprises a plurality of consecutive nucleotides, the plurality of consecutive nucleotides, wherein all cytosine bases in the adaptor polynucleotides are methylated and wherein each of the adaptor polynucleotides comprises a region of double stranded nucleic acids and at least one region of single stranded nucleic acids, the region of single-stranded nucleic acids forming a forked end; and
   the plurality of consecutive nucleotides is complementary to the last 21 consecutive nucleotides of SEQ ID NO: 6.

2. The kit of claim 1, wherein the at least one region of single stranded nucleic acids comprises the plurality of consecutive nucleotides.

3. The kit of claim 1, wherein the region of double stranded nucleic acids comprises 5 or more consecutive base pairs.

4. The kit of claim 1, wherein the adaptor polynucleotides are phosphorylated at a 5' end of the region of double stranded nucleic acids.

5. The kit of claim 1, wherein the kit comprises two or more amplification primers, at least one of the amplification primers comprising a region that hybridizes to the at least one region of single stranded nucleic acids.

6. The kit of claim 1, wherein the kit comprises two or more amplification primers, at least one of the amplification primers comprising a region that extends beyond a 5' end of the at least one region of single stranded nucleic acids.

7. The kit of claim 1, wherein the kit comprises two or more amplification primers, at least one of the amplification primers comprising a region that hybridizes to, and extends beyond, a 5' end of the at least one region of single stranded nucleic acids.

8. The kit of claim 1, wherein the kit comprises first oligonucleotide primers configured to anneal to the adaptor polynucleotides and second oligonucleotide primers configured to anneal to a region of extended strands produced by extension of the first oligonucleotide primers.

9. The kit of claim 8, wherein the first oligonucleotide primers and the second oligonucleotide primers are capable of annealing to one strand in the region of double stranded nucleic acids of the adaptor polynucleotides.

10. The kit of claim 9, wherein the first oligonucleotide primers and the second oligonucleotide primers comprise one or more of SEQ ID NO: 3 and SEQ ID NO: 4.

11. The kit of claim 1, wherein the adaptor polynucleotides comprise forked universal adaptors.

12. The kit of claim 1, wherein the adaptor polynucleotides comprise universal adaptors.

13. The kit of claim 1, further comprising oligonucleotide primers capable of annealing to the adaptor polynucleotides.

14. The kit of claim 13, wherein the oligonucleotide primers are configured to anneal to at least one region of single stranded nucleic acids of the adaptor polynucleotides.

15. The kit of claim 1, wherein the adaptor polynucleotides comprise one or more of SEQ ID NO: 1 and SEQ ID NO: 2.

16. A method of analysing methylation status of cytosine bases in a nucleic acid, comprising:
   (a) providing a sample of double stranded nucleic acid target fragments derived from said nucleic acid;
   (b) ligating universal adaptors to the double stranded nucleic acid target fragments to produce adaptor-ligated double stranded nucleic acid target fragments, wherein:
      cytosine bases in the universal adaptors are methylated,
      each of the universal adaptors comprises a plurality of consecutive nucleotides,
      wherein each of the universal adaptors comprises a region of double stranded nucleic acids and at least one region of single stranded nucleic acids, the region of single-stranded nucleic acids forming a forked end, and
      the plurality of consecutive nucleotides is complementary to nucleotides in the last 21 consecutive nucleotides of SEQ ID NO: 6;
   (c) treating the adaptor-ligated double stranded nucleic acid target fragments with a reagent that converts non-methylated cytosine bases to uracil to produce a treated sample of adaptor-ligated double stranded nucleic acid target fragments;
   (d) sequencing the treated adaptor-ligated double stranded nucleic acid target fragments; and
   (e) analysing sequences of the treated sample to determine which cytosine bases were converted to uracil bases, thereby determining the methylation status of the nucleic acid.

\* \* \* \* \*